United States Patent [19]

Cragoe, Jr. et al.

[11] 4,356,314

[45] Oct. 26, 1982

[54] [5,6,9A-SUBSTITUTED-3-OXO-1,2,9,9A-TETRAHYDRO-3H-FLUOREN-7-YL)OXY]ALKANOIC AND CYCLOALKANOIC ACIDS, THEIR ANALOGS, ESTERS, SALTS, AND DERIVATIVES

[75] Inventors: Edward J. Cragoe, Jr., Lansdale; Gerald E. Stokker, Gwynedd Valley; Norman P. Gould, Lansdale, all of Pa.

[73] Assignee: Merck & Co., Inc., Rahway, N.J.

[21] Appl. No.: 236,076

[22] Filed: Feb. 19, 1981

Related U.S. Application Data

[63] Continuation-in-part of Ser. No. 164,754, Jun. 30, 1980, and a continuation-in-part of Ser. No. 86,625, Oct. 19, 1979.

[51] Int. Cl.³ .............................................. C07C 69/94
[52] U.S. Cl. ......................................... 560/53; 424/260; 424/250; 424/262; 424/263; 424/267; 424/274; 424/275; 424/285; 424/308; 424/309; 424/317; 424/324; 260/463; 544/155; 544/294; 544/380; 546/194; 546/285; 548/201; 548/346; 548/573; 549/29; 549/501; 562/461
[58] Field of Search ................. 560/53; 260/326.43, 260/347.3, 347.4, 463; 544/155, 294, 380; 546/194, 285; 548/201, 346; 549/29; 562/461; 424/248.54, 248.55, 260, 250, 262, 263, 267, 274, 275, 285, 308, 309, 317, 324

[56] References Cited

U.S. PATENT DOCUMENTS

| | | | |
|---|---|---|---|
| 3,639,624 | 2/1972 | Shen et al. | 562/461 |
| 3,704,314 | 11/1972 | Cragoe et al. | 560/53 |
| 3,819,693 | 6/1974 | Levine et al. | 560/53 |
| 3,856,977 | 12/1974 | Stiller et al. | 562/461 |
| 3,903,145 | 9/1975 | Levine et al. | 560/53 |
| 3,933,905 | 1/1976 | Brunet | 562/461 |
| 3,974,212 | 8/1976 | Cragoe et al. | 560/53 |
| 4,070,460 | 1/1978 | Galner | 424/130 |
| 4,096,267 | 6/1978 | Cragoe, Jr. et al. | 424/262 |

FOREIGN PATENT DOCUMENTS 1244762  7/1967  Fed. Rep. of Germany ........ 560/53

OTHER PUBLICATIONS deSolms, S. J. et al., Journal of Med. Chem., 21, 437 (1978).
Gaab, M., Journal of Neurol. 220, 185–197 (1979).
Kumar, A. M. et al., Journal Physiol. (1977) 272, pp. 563–572.
Hartman, A. et al., Arch. Psychiat. Nervenkr. 224, 351–360 (1977).
Tornheim, P. A., Anatomical Record, 19, Oct. 1978.

*Primary Examiner*—Paul J. Killos
*Attorney, Agent, or Firm*—Edmunde D. Riedl; Mario A. Monaco

[57] ABSTRACT

The invention relates to novel [(5,6,9a-substituted-3-oxo-1,2,9,9a-tetrahydro-3H-fluoren-7-yl)oxy]alkanoic and cycloalkanoic acids, and their analogs, esters, salts and derivatives. These compounds are synthesized by methods selected from a number of synthetic routes depending on the particular structure, choice of intermediate or preferred reaction sequence. The compounds are useful in the treatment and prevention of injury to the brain and spinal chord due to accidents, ischemic stroke and hydrocephalus; compositions for such uses are also disclosed.

15 Claims, No Drawings

4,356,314

[5,6,9A-SUBSTITUTED-3-OXO-1,2,9,9A-TETRAHYDRO-3H-FLUOREN-7-YL)OXY]ALKANOIC AND CYCLOALKANOIC ACIDS, THEIR ANALOGS, ESTERS, SALTS, AND DERIVATIVES

This is a c-i-p of S.N. 06/086625 filed 10/19/1979 now abandoned which is a c-i-p of S.N. 06/164,754 filed 06/30/80 now abandoned.

BACKGROUND OF THE INVENTION

Trauma to the brain or spinal chord caused by physical forces acting on the skull or spinal column, by ischemic stroke or by hydrocephalus results in edema and swelling of the affected tissues. This is followed by ischemia, temporary or permanent brain and/or spinal chord injury and may result in death. The tissues mainly affected are classified as grey matter, more specifically astroglial cells.

The specific therapy currently used for the treatment of the medical problems described is limited to steroids, such as, the sodium salt of 6-α-methylprednisolone succinate. Although these agents are effective in situations involving white matter edema, they comprise relative ineffective therapy for grey matter edema. Thus, the compounds of this invention comprise a novel and specific treatment for a medical problem where no specific therapy is available.

The compounds of the invention have the added advantage of being devoid of the toxic side effects of the steroids and of having little or no renal effects.

DESCRIPTION OF THE INVENTION

The compounds of the instant invention are best characterized by reference to the following structural formula:

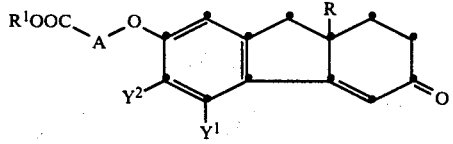

wherein R is H, lower alkyl, branched or unbranched, such as methyl, ethyl, propyl, isopropyl, butyl, sec. butyl, isobutyl and the like; lower alkenyl, such as vinyl and allyl; lower alkynyl, such as propargyl; aryl, such as phenyl; aryl lower alkyl, such as benzyl; lower cycloalkyl, such as cyclopropyl and cyclobutyl, lower cycloalkyl lower alkyl, such as cyclopropylmethyl and the like;

$R^1$ is H, lower alkyl, such as methyl, ethyl, propyl, isopropyl, butyl, isobutyl, tert-butyl and the like; lower alkenyl, such as, allyl, 2-butenyl, and like; lower alkynyl, such as, propargyl, butynyl and the like; lower cycloalkyl, such as cyclobutyl, cyclopentyl and the like; substituted lower alkyl, where the substituent is carboxy, lower alkoxycarbonyl, oxo, hydroxy, lower alkoxy, halo, lower acyloxy, lower dialkylamino, sulfamoyl, pyridyl, furyl, tetrahydrofuryl, aryl, 1-methylpiperidyl, morpholinyl, pyrrolidinyl, 1-methylpiperazinyl, thienyl, and the like; substituted cycloalkyl, such as carboxycycloalkyl; and the like; heterocyclic, such as, imidazolyl, pyridyl, thiazolyl, pyrazinyl, furyl, and the like; aryl, such as phenyl, carboxyphehyl, hydroxymethylphenyl and the like;

where $R^2$ is H, methyl or ethyl, $R^3$ is H, F or methyl and $R^2$ and $R^3$ may be joined together to form a ring which can be represented by $>C(CH_2)_n$ where n=2, 3, or 4.

Since the 9a carbon atom in the molecule is asymmetric, the compounds of the invention are racemic; however, these compounds can be resolved, so that the invention includes the pure enantiomers. In addition, in some instances, the group represented by A and by $R^1$ includes an asymmetric carbon atom. Thus, these molecules may contain two or three asymmetric carbon atoms and now can consist of two or four diastereomers, each of which consists of two enantiomers. The invention includes each diastereomer and their enantiomers whenever they exist.

Although the invention involves novel [(5,6,9a-substituted-3-oxo-1,2,9,9a-tetrahydro-3H-fluoren-7-yl)oxy]-alkanoic and cycloalkanoic acids, it also includes the obvious analogs, the corresponding esters, salts and their derivatives such as anhydrides, amides, hydrazides, guanidides and the like.

PREFERRED EMBODIMENTS OF THE INVENTION

The preferred embodiments of the instant invention are realized in structural formula IA wherein:

R is lower alkyl, alkenyl, alkynyl, cyclopropyl, cyclopropylmethyl, or aralkyl

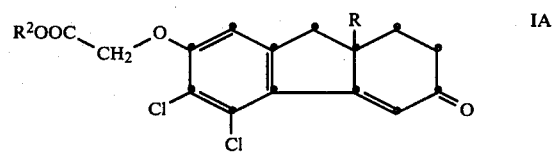

$R^2$ is hydrogen, lower alkyl, substituted alkyl, such as carboxyalkyl, hydroxyalkyl, dihydroxyalkyl, trihydroxyalkyl, oxoalkyl, dilower alkylaminoalkyl, and heterocyclic-alkyl.

$Y^1$ and $Y^2$ are chloro

Also included are the enantiomers of each racemic compound.

A preferred compound is [(5,6-dichloro-9a-methyl-3-oxo-1,2,9,9a-tetrahydro-3H-fluoren-7-yl)oxy]-acetic acid.

Another preferred compound is [(5,6-dichloro-9a-ethyl-3-oxo-1,2,9,9a-tetrahydro-3H-fluoren-7-yl)oxy]-acetic acid and its enantiomers.

Another preferred compound is [(5,6-dichloro-3-oxo-9a-propyl-1,2,9,9a-tetrahydro-3H-fluoren-7-yl)oxy]-acetic acid and its enantiomers.

Another preferred compound is [(5,6-dichloro-3-oxo-9a-isopropyl-1,2,9,9a-tetrahydro-3H-fluoren-7-yl)oxy]acetic acid.

Another preferred compound is [(9a-butyl-5,6-dichloro-3-oxo-1,2,9,9a-tetrahydro-3H-fluoren-7-yl)oxy]acetic acid and its enantiomers.

Another preferred compound is [(5,6-dichloro-3-oxo-9a-vinyl-1,2,9,9a-tetrahydro-3H-fluoren-7-yl)oxy]acetic acid.

Another preferred compound is [(9a-allyl-5,6-dichloro-3-oxo-1,2,9,9a-tetrahydro-3H-fluoren-7-yl)oxy]acetic acid and its enantiomers.

Another preferred compound is [(5,6-dichloro-3-oxo-9a-propargyl-1,2,9,9a-tetrahydro-3H-fluoren-7-yl)oxy]acetic acid and its enantiomers.

Another preferred compound is [(5,6-dichloro-9a-tetrahydro-3H-fluoren-7-yl)oxy]acetic acid and its enantiomers.

Another preferred compound is [(5,6-dichloro-9a-cyclopropylmethyl-3-oxo-1,2,9,9a-tetrahydro-3H-fluoren-7-yl)oxy]acetic acid and its enantiomers.

Another preferred compound is [(9a-benzyl-5,6-dichloro-3-oxo-1,2,9,9a-tetrahydro-3H-fluoren-7-yl)oxy]acetic acid and its enantiomers.

Another preferred compound is 1-carboxyl-1-methylethyl [(5,6-dichloro-9a-methyl-3-oxo-1,2,9,9a-tetrahydro-3H-fluroen-7-yl)oxy]acetate and its enantiomers.

Another preferred compound is 1-carboxy-1-methylethyl [(5,6-dichloro-9a-ethyl-3-oxo-1,2,9,9a-tetrahydro-3H-fluoren-7-yl)oxy]acetate.

Another preferred compound is 1-carboxy-1-methylethyl [(5,6-dichloro-9a-isopropyl-3-oxo-1,2,9,9a-tetrahydro-3H-fluoren-7-yl)oxy]acetate.

Another preferred compound is 1-carboxy-1-methylethyl [(5,6-dichloro-3-oxo-9a-propyl-1,2,9,9a-tetrahydro-3H-fluoren-7-yl)oxy]acetate and its enantiomers.

Another preferred compound is 1-carboxy-1-methylethyl [(9a-butyl-5,6-dichloro-3-oxo-1,2,9,9a-tetrahydro-3H-fluoren-7-yl)oxy]acetate and its enantiomers.

Another preferred compound is 1-carboxy-1-methylethyl [(5,6-dichloro-3-oxo-9a-vinyl-1,2,9,9a-tetrahydro-3H-fluoren-7-yl)oxy]acetate.

Another preferred compound is 1-carboxyl-1-methyethyl [(9a-allyl-5,6-dichloro-3-oxo-1,2,9,9a-tetrahydro-3H-fluoren-7-yl)oxy]acetate and its enantiomers.

Another preferred compound is 1-carboxy-1-methylethyl [(5,6-dichloro-3-oxo-9a-propyl-1,2,9,9a-tetrahydro-3H-fluoren-7-yl)oxy]acetate and its enantiomers.

Another preferred compound is 1-carboxy-1-methylethyl [(5,6-dichloro-9a-cyclopropyl-3-oxo-1,2,9,9a-tetrahydro-3H-fluoren-7-yl)oxy]acetate and its enantiomers.

Another preferred compound is 1-carboxy-1-methylethyl [(5,6-dichloro-9a-cyclopropylmethyl-3-oxo-1,2,9,9a-tetrahydro-3H-fluoren-7-yl)oxy]acetate and its enantiomers.

Another preferred compound is 1-carboxy-1-methylethyl [(9a-benzyl-5,6-dichloro-3-oxo-1,2,9,9a-tetrahydro-3H-fluoren-7-yl)oxy]acetate and its enantiomers.

Another preferred compound is ethyl [(5,6-dichloro-9a-ethyl-3-oxo-1,2,9,9a-tetrahydro-3H-fluoren-7-yl)oxy]acetate and its enantiomers.

Another preferred compound is 3-pyridylmethyl-[(5,6-dichloro-9a-ethyl-3-oxy-1,2,9,9a-tetrahydro-3H-fluoren-7-yl)oxy]acetate and its enantiomers.

Another preferred compound is 2-oxopropyl [(5,6-dichloro-9a-ethyl-3-oxo-1,2,9,9a-tetrahydro-3H-fluoren-7-yl)oxy]acetate and its enantiomers.

Another preferred compound is 2-(dimethylamino)-ethyl [(5,6-dichloro-9a-ethyl-3-oxo-1,2,9,9a-tetrahydro-3H-fluoren-7-yl)oxy]acetate and its enantiomers.

Another preferred compound is 3-carboxypropyl [(5,6-dichloro-9a-ethyl-3-oxy-1,2,9,9a-tetrahydro-3H-fluoren-7-yl)oxy]acetate and its enantiomers.

Another preferred compound is carboxymethyl [(5,6-dichloro-9a-ethyl-3-oxo-1,2,9,9a-tetrahydro-3H-fluoren-7-yl)oxy]acetate.

Another preferred compound is 3-hydroxypropyl [(5,6-dichloro-9a-ethyl-3-oxo-1,2,9,9a-tetrahydro-3H-fluoren-7-yl)oxy]acetate.

Another preferred compound is [(5,6-dichloro-9a-ethyl-3-oxo-1,2,9,9a-tetrahydro-3H-fluoren-7-yl)oxy]acetic acid hydrazide.

Especially preferred are the (+)R enantiomers of the racemic modification of each compound; thus, the most preferred compounds are the (+)R enantiomers of the compounds tested supra.

Included within the scope of this invention are the analogs and derivatives of the parent carboxylic acids, their salts, their esters and their amides and other derivatives which may be prepared by conventional methods well known to those skilled in the art.

Thus, the acid addition salts can be prepared by the reaction of the carboxylic acids of the invention with an appropriate amine, guanidine, ammonium hydroxide, alkali metal hydroxide, alkali metal bicarbonate or alkali metal carbonate and the like. The salts are selected from among the non-toxic, pharmaceutically acceptable bases.

The synthesis of the carboxylic acid compounds of Formula II is generally carried out by the hydrolysis of the corresponding ester (III):

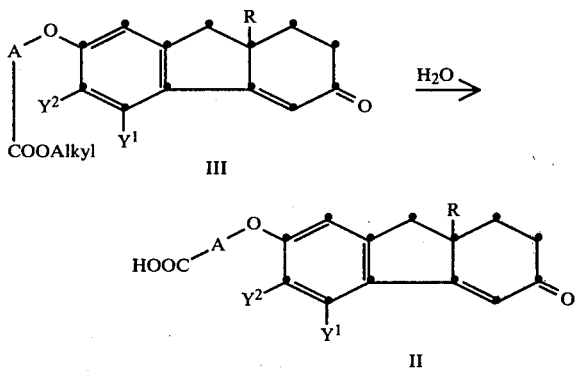

The process can be effected by heating the ester in a solution of acetic and aqueous inorganic acid, such as hydrochloric acid, sulfuric acid and the like. The hydrolysis also can be effected in aqueous alcoholic base such as sodium hydroxide or potassium hydroxide in aqueous methanol or ethanol. The product is recovered by acidification with an acid, such as, hydrochloric acid. The reaction can be carried out at temperatures of 30° C. to 100° C. for periods of about 20 minutes to 6 hours, depending on the specific ester used and the other reaction conditions. In the instances, such as where A is —CHF—, it is advantageous to carry out the hydrolysis using a weak base, such as aqueous sodium bicarbonate. A solvent, such as aqueous ethanol, methanol or isopropyl alcohol is used and the mixture heated to 45° C. to 100° C. for periods of 15 minutes to 4 hours. Acidification of the reaction mixture with strong aqueous acids, such as hydrochloric acid, hydrobromic acid or sulfuric acid produces the desired compound of Formula II.

A second method for the preparation of compounds of the type illustrated by Formula II involve the reaction of a haloalkanoic or halocycloalkanoic acid (X—A—COOH) with the appropriate phenol (IV).

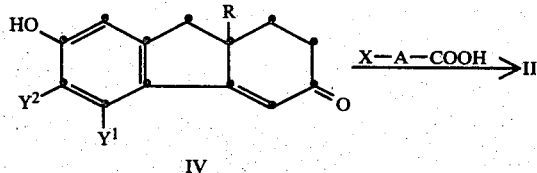

Using a haloalkanoic or halocycloalkanoic acid X—A—COOH, where X=iodo, bromo or chloro and A is as defined above, for example, iodoacetic acid or bromofluoroacetic acid, as the etherification agent, the reaction is conducted in the presence of a base. The base is selected from among the alkaline earth or alkali metal bases such as sodium or potassium carbonate, calcium hydroxide and the like. The reaction is carried out in a liquid reaction milieu, the choice being based on the nature of the reactants; however, solvents which are reasonably inert to the reactants and are fairly good solvents for the compounds of Formula IV and the X—A—COOH reagent, can be used. Highly preferable are dimethylformamide, ethanol, acetone, and N-methylpyrrolidine-2-one, and the like.

A third method for preparing compounds of Formula II involves the pyrolysis of the corresponding tert.-butyl ester (IB):

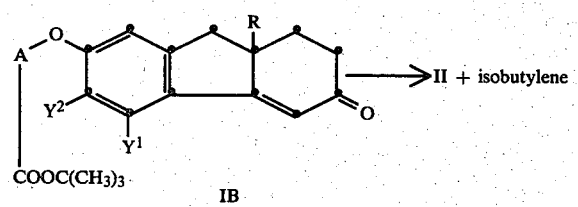

This method involves heating a tert.-butyl ester of the type illustrated by formula IB at from about 80° C. to 120° C. in a suitable nonaqueous solvent in the presence of catalytic amount of a strong acid. The solvents are generally selected from among the type benzene, toluene, xylene, etc. and the acid catalyst may be a strong organic or inorganic acid, such as p-toluenesulfonic acid, benzenesulfonic acid, methanesulfonic acid, sulfuric etc. The acid, being a catalyst, is generally used in relatively small quantities as compared to the tert.-butyl ester (IB). It is to be noted that this reaction is a pyrolysis and not a hydrolysis, since water is excluded from the reaction and the products are a carboxylic acid (Formula II) and isobutylene and no alcohol is produced.

Another method of converting compounds of Type IB to those of Type II is by heating compounds of type IB with trifluoroacetic acid in a solvent like dichloromethane.

A fourth method is limited to the instances wherein compounds of Formula IIA are produced, i.e., where A is ethylene:

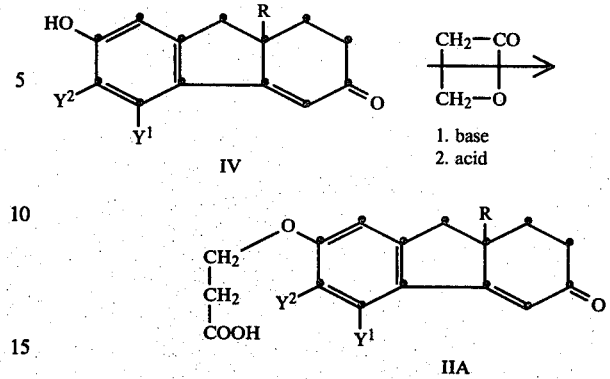

This synthesis involves the reaction of the appropriate phenol (IV) with propiolactone in the presence of a base and a solvent, preferably while heating and stirring the reaction mixture. Solvents, such as a mixture of water and an alcohol, such as methanol, ethanol or propanol are used. The base is selected from among the alkali metal hydroxides or carbonates, such as sodium hydroxide, potassium hydroxide, potassium carbonate and the like. The temperature is generally at the boiling point of the solvent mixtures but it may be at 50° C.-110° C. depending on the reactants involved. The product is isolated by acidification of the reaction mixture with a strong acid such as hydrochloric or sulfuric acid.

Special methods are used to synthesize compounds of Formula II where R is vinyl (Formula IIB) or cyclopropyl (Formula IIC).

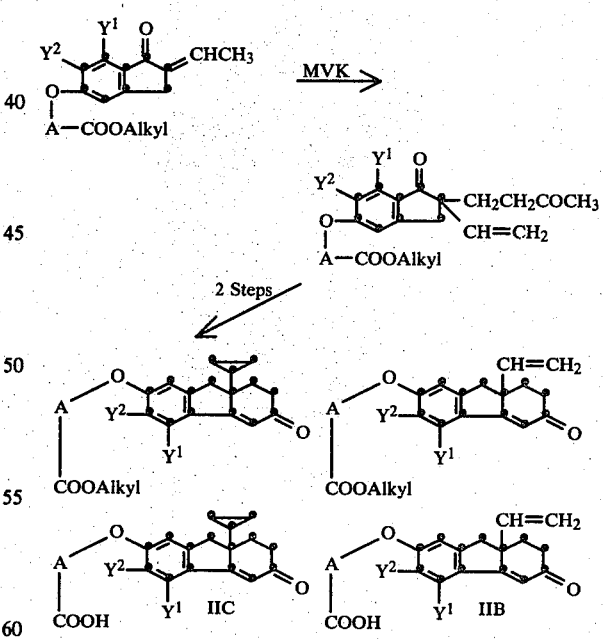

An alkyl [(2-ethylidene-1-oxo-2,3-dihydro-1H-indene-5-yl)oxy]alkanoate is treated with methyl vinyl ketone (MVK) in the presence of a base, such as, potassium tert.-butoxide, in 1,2-dimethoxyethane at 0° C. or lithium dimethylamide at −70° C. in tetrahydrofuran. The reaction is conducted in an atmosphere of dry nitrogen.

The alkyl [[1-oxo-2-(3-oxobutyl)-2-vinyl-2,3-dihydro-1H-inden-5-yl]oxy]alkanoate produced is cyclized to an alkyl [(3-oxo-9a-vinyl-1,2,9,9a-tetrahydro-3H-fluoren-7-yl)oxy]alkanoate by heating in the presence of a reagent like pyrrolidine acetate and the like in benzene or toluene. Heating with a base, such as, potassium tert.-butoxide in tert.-butyl alcohol is also effective.

Finally, the compound of Formula IIB is produced by saponification of the alkyl [(3-oxo-9a-vinyl-1,2,9,9a-tetrahydro-3H-fluoren-7-yl)oxy]alkanoate by heating with a base, such as, sodium or potassium hydroxide in a solvent, such as water or a mixture of methanol or ethanol and water. The product is generated upon acidification with an acid, such as, hydrochloric or sulfuric acid.

Alternatively, compounds of Formula IIB can be generated directly from an alkyl [[1-oxo-2-(3-oxobutyl)-2-vinyl-2,3-dihydro-1H-inden-5-yl]oxy]alkanoate by dissolving in a mixture of an alcohol, such as, methanol or ethanol and aqueous sodium hydroxide or potassium hydroxide. After standing at ambient temperature for 24 to 48 hours, the product is isolated by acidification with an acid, such as, hydrochloric or sulfuric acid.

The preparation of compounds of Formula IIC is carried out by treating an alkyl [(3-oxo-9a-vinyl-1,2,9,9a-tetrahydro-3H-fluoren-7-yl)oxy]alkanoate with a zinc-copper couple and methylene iodide in a solvent, such as, ethyl ether, tetrahydrofuran or 1,2-dimethoxyethane at ambient temperature for an hour according to the conditions of the Simmons-Smith reaction. The alkyl [(3-oxo-9a-cyclopropyl-1,2,9,9a-tetrahydro-3H-fluoren-7-yl)oxy]acetate is then hydrolyzed to a compound of Formula IIC by heating with an aqueous-alcoholic solution of a base, such as, potassium hydroxide or sodium hydroxide followed by acidification with an acid, such as, hydrochloric or sulfuric acid.

Alternatively, a compound of Formula IIC can be produced by treating an alkyl [[1-oxo-2-(3-oxobutyl)-2-vinyl-2,3-dihydro-1H-inden-5-yl]oxy]alkanoate with zinc-copper couple and methylene iodide in tetrahydrofuran to give an alkyl [[1-oxo-2-(3-oxobutyl)-2-cyclopropyl-2,3-dihydro-1H-inden-5-yl]oxy]alkanoate which is then cyclized and finally hydrolyzed by the methods just described. Likewise, the alkyl [[1-oxo-2-(3-oxobutyl)-2-cyclopropyl-2,3-dihydro-1H-inden-5-yl]oxy]alkanoate may be converted directly to IIC by treatment with aqueous methanolic sodium hydroxide followed by acidification with hydrochloric acid.

The preparation of compound IV can be carried out by one or the other of two methods. The first method involves the following three-step process:

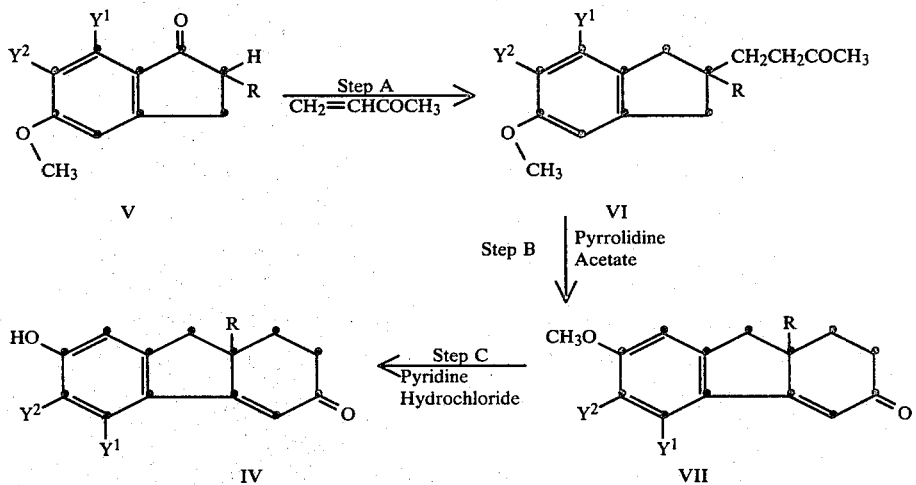

Compounds of the type represented by Formula V which are used to produce the compounds of this invention have generally been described in the scientific and/or patent literature. For those that have not been previously disclosed or must be prepared by new methods, a description of their synthesis will be described later.

The first step (Step A) in the synthesis involves the reaction of a compound of Formula V with methyl vinyl ketone to produce a compound of Formula VI. The reaction is catalyzed by a base, such as triton B (benzyltrimethylammonium hydroxide) in methanol but other bases such as tetramethylammonium hydroxide, tetraethylammonium hydroxide or sodium methoxide are effective catalysts. Solvents which are inert to the reaction and are effective in dissolving the reactants and product are normally used. Tetrahydrofuran is an especially preferred solvent but others, like p-dioxane or 1,2-dimethoxyethane can be used. The reaction is generally conducted at ambient temperatures but temperatures in the range of 10° C. to 45° C. or somewhat above or below these values can be used.

The second step (Step B) in the synthesis is the cyclization of a compound of Formula VI to give a compound of Formula VII. The reaction is generally conducted in the presence of a solvent such as benzene, toluene, xylene, anisole and the like but many other solvents which are inert to the reactants and to the catalyst are useful. A catalyst is necessary for increasing the rate of reaction. Salts of weak organic acids and weak inorganic or organic bases are preferred; for example, pyrrolidine acetate, piperidine acetate, pyrrolidine propionate and the like. The reaction is preferably conducted at the temperature of the boiling solvent but temperature of 30° C.–120° C. can be used. It is advantageous to carry out the reaction under conditions in which the water produced in the reaction is constantly removed. This is effected by various means, such as using a Dean-Stark constant water separator or co-distilling the solvent and the water. Another device for removing the water is to add molecular sieves designed for removing water, for example, Davison Molecular Sieves of 3A size M-564 (Cation: potassium, base:alumina-silicate).

In some instances, bases, such as potassium tert.-butoxide in tert.-butyl alcohol or potassium hydroxide or sodium hydroxide in aqueous methanol or ethanol may be used to effect cyclization.

The last step (Step C) involves the ether cleavage of a compound of Formula VII to produce a compound of Formula IV. This can be accomplished by many of the agents known to cleave ethers, especially useful are hydrohalide salt of weak bases, such as pyridine hydrochloride or pyridine hydrobromide, but other agents, such as aqueous hydrobromic acid or aluminum bromide can be used. When pyridine hydrohalides are used, the temperatures above that which these substances melt are generally employed. This usually involves temperatures in the range of 150° C. to 215° C., but temperatures somewhat lower or higher can be used. The period of heating varies depending on the specific compound but periods of from 15 minutes to 2 hours may be used.

The second method for preparing compounds of Formula IV is shown by the five-step reaction illustrated below. It should be mentioned that this is not simply a cyclical method whereby a compound of the invention (Formula II) is converted to one of its precursors (Formula IV) simply to be reconverted to the product again (Formula II).

In this instance, a readily accessible compound of Formula VIII, for example, where the A moiety is $CH_2$, is converted to a compound of Formula II which, in turn, is converted to a compound of Formula IV which now can be used to synthesize a compound of Formula II which is difficulty accessible, i.e, wherein A is —CHF—, $>C(CH_3)_2$, or $>C(CH_2)_3$.

be effected by many of the known methods. Especially useful is the procedure whereby compound of Formula VIII is reacted with an alkyl halide, such as methyl iodide, in the presence of an alkaline earth or alkali metal carbonate, such as potassium carbonate or sodium carbonate in the presence of a solvent such as dimethylformamide, 1-methylpyrrolidin-2-one, and the like to produce a compound of Formula IX. The reaction is generally conducted at a temperature of 30° C.–60° C. for from 3 to 20 hours. Alternatively, the esterification may be effected by the reaction of a compound of Formula VIII with an alkanol, such as methanol, ethanol or isopropyl alcohol in the presence of an acid catalyst. The acid catalyst may be a strong organic or inorganic acid, such as sulfuric acid, hydrochloric acid, p-toluenesulfonic acid and the like.

The second step (Step B) involves the reaction of a compound of Formula IX with methyl vinyl ketone to form a compound of Formula X. The conditions for this reaction are similar to those described above for the conversion of a compound of Formula V to one of Formula VI.

The third step (Step C) is the cyclization of compounds of Formula X to form those of Formula IC. The conditions for this reaction are similar to those described for the conversion of compounds of Formula VI to those of Formula VII.

The fourth step (Step D) is the hydrolysis of compounds of Formula IC to those of Formula II. The conditions of this reaction have been described earlier.

The final step (Step E) is the ether cleavage of a compound of Formula II to produce a compound of Formula IV. The conditions for this reaction are similar to those described for the conversion of a compound of Formula VII to those of Formula IV.

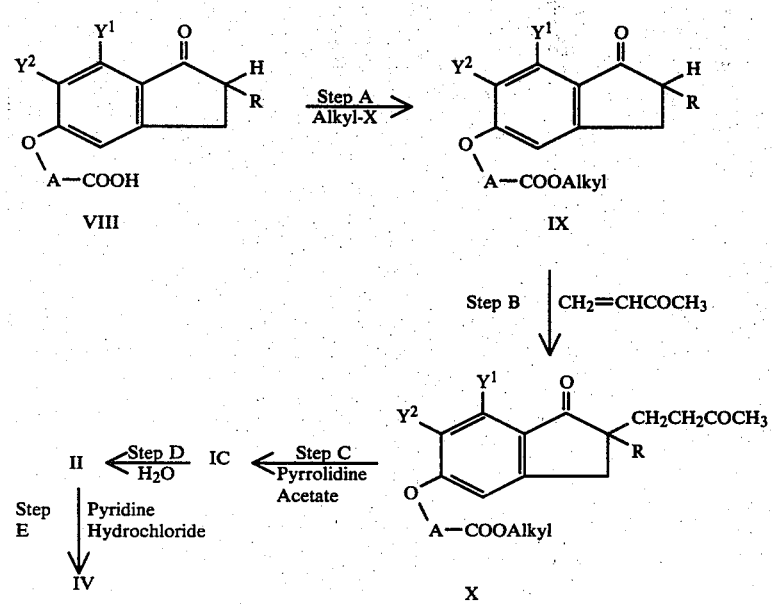

The first step (Step A) involves the esterification of compound of Formula VIII to produce the ester of Formula IX. The starting material, Formula VIII, is generally known; however, the synthesis of those which are not known or are accessible only by new methods will be discussed later. The esterification can As indicated earlier, those compounds of Formula V and Formula VIII which are not known or are accessible only by new synthetic routes, may be prepared by methods disclosed in this invention which are illustrated below.

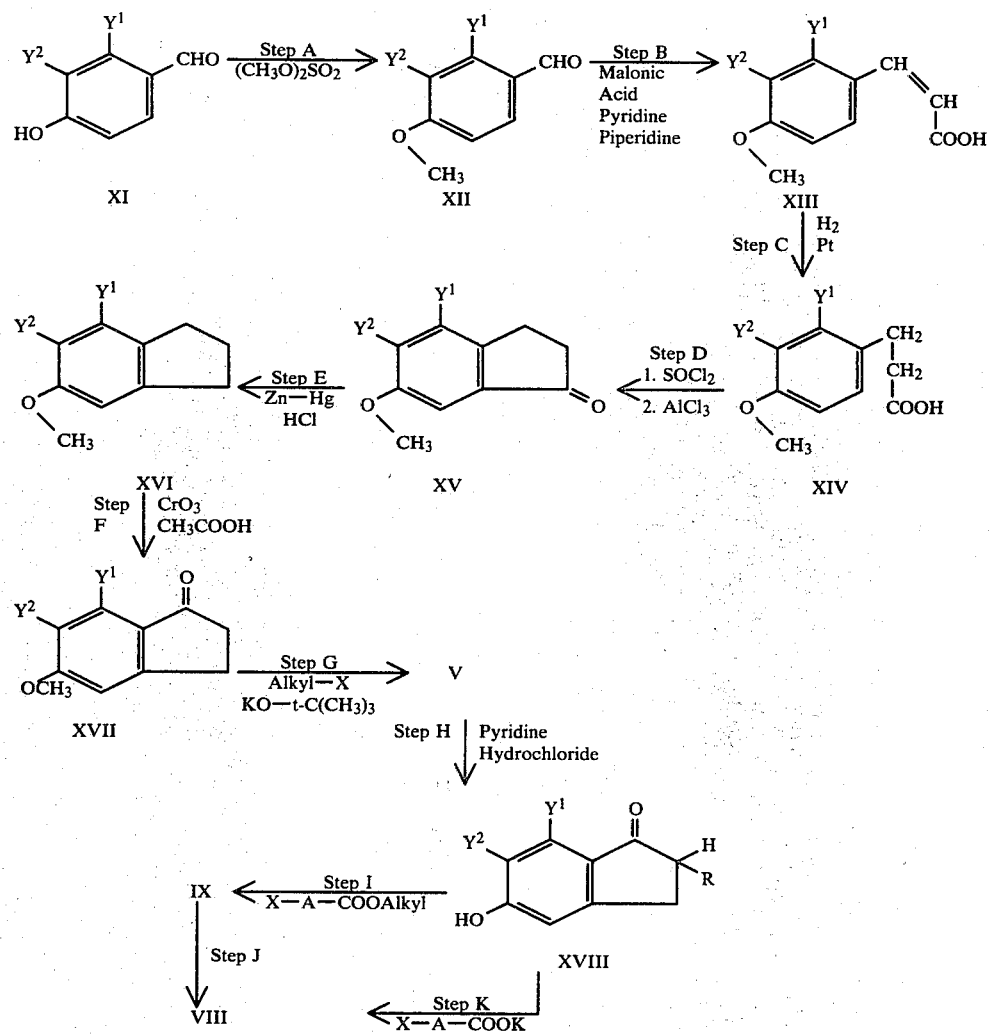

The first step is the etherification of a compound of Formula XI to produce a compound of Formula XII. This is accomplished by a reaction involving a compound of Formual XI in any one of a number of chemical processes; especially useful is dimethyl sulfate in the presence of potassium carbonate using a solvent, such as dimethylformamide.

The second step (Step B) is the conversion of a compound of Formula XII to one of Formula XIII. This can be accomplished by one or another of many methods; especially useful is the reaction of a compound of Formula XII with malonic acid in the presence of a solvent such as pyridine and a weak organic base, such as piperidine or pyrrolidine. The reaction is effected by heating for 1 to 6 hours at a temperature of 75° C. to 120° C., preferably at about 95° C. to 100° C. Quenching the reaction mixture in ice and acidification with a strong acid, such as hydrochloric acid yields the desired compound of Formula XIII.

The third step (Step C) involves the catalytic hydrogenation of a compound of Formula XIII to produce a compound of Formula XIV. The reduction is conducted in an atmosphere of hydrogen at an initial pressure of 10 to 100 psi and at temperatures of from 15° C. to 45° C. A solvent in which the starting material and product are reasonably soluble and which is inert to the reactants, product and catalyst is employed. Solvents such as tetrahydrofuran, dioxane, and the like are especially useful. The catalyst is usually a finely divided noble metal (which may be on an inert support) i.e., palladium on charcoal or it may be a noble metal derivative which upon exposure to hydrogen is reduced to the free metal, i.e., platinum oxide.

The fourth step (Step D) consists of the cyclization of a compound of Formula XIV to produce a compound of Formula XV. This is accomplished by first converting a compound of Formula XIV to the corresponding acid chloride using a reagent like thionyl chloride or phosphorus oxychloride. A solvent, such as benzene is advantageous. The acid chloride is subjected to the conditions of the Friedel-Crafts reaction which results in the cyclization of the acid chloride to form a compound of Formula XV. A reagent such as aluminum chloride, stannic chloride and the like are used to effect the cyclization. The reaction is conducted in a typical Friedel-Crafts solvent, such as methylene chloride or carbon disulfide. The reaction time is generally 1 to 6 hours.

The fifth step (Step E) involves the reduction of a compound of Formula XV to one of Formula XVI. This reaction is accomplished by using zinc amalgam and hydrochloric acid. The reaction is generally conducted in a solvent such as a mixture of water and an alkanol, such as ethanol or 1-propanol. The reaction time is generally between 3 and 10 hours and is generally conducted at temperatures of 60° C. to 110° C. The time and temperature are interdependent so that when the temperature is lower, the time is longer.

The sixth step (Step F) involves the oxidation of a compound of formula XVI to produce one of Formula XVII. The oxidation is best accomplished using a reagent such as chromium trioxide in a mixture of acetic acid and water. The reaction is advantageously conducted at ambient temperatures but temperatures somewhat higher or lower may be used.

The seventh step (Step G) consists of the alkylation of a compound of Formula XVII to produce one of Formula V. This first involves formation of the anion of a compound of Formula XVII by treatment with a base, such as an alkali metal alkoxide, for example, potassium tert.-butoxide in tert.-butyl alcohol. An alkali metal hydride, such as sodium hydride and the like, or an alkali metal amide, such as sodium amide, lithium amide and the like, also may be used. The anion is then treated with an alkylating agent, Alkyl-X. Solvents which are inert to the reactants may be employed. Suitable solvents are 1,2-dimethoxyethane, tert.-butyl alcohol, dimethylformamide, benzene and the like. The reaction is conducted at a temperature in the range from about 25° C. to about 150° C.

The eighth step (Step H) consists of the ether cleavage of a compound of Formula V to produce one of Formula XVIII. This reaction is carried out under conditions similar to those described earlier for the conversion of compounds of Formula VII to those of Formula IV.

The ninth step (Step I) consists of the etherification of a compound of Formula XVIII to one of Formula IX. This reaction is carried out under conditions described for the conversion of compounds of Formula IV to those of Formula IC.

Compound VIII may be prepared by one of two methods. The first method (Step J) involves the hydrolysis or pyrolysis of a compound of Formula IX to produce one of Formula VIII. This reaction is carried out by the methods described for the conversion of compounds of Formula IC or ID to those of Formula II.

The second method for the preparation of compounds of Formula VIII is the etherification of compounds of Formula XVIII. This reaction is carried out by the methods described for the conversion of compounds of Formula IV to those of Formula II.

As mentioned earlier, the compounds of this invention possess one and sometimes two or three asymmetric carbon atoms. In the instances where they posssess two or three asymmetric carbon atoms, the reaction whereby these chiral centers are established can produce two or four diastereomers. These may be separated to obtain each pure diastereomer by methods well known to those skilled in the art, such as by fractional crystallization, column chromatography, high pressure liquid chromatography and the like.

Those compounds possessing only one asymmetric carbon atom, as well as each pure diastereomer from compounds possessing two or three asymmetric carbon atoms, consist of a racemate composed of two enantiomers. The resolution of the two enantiomers may be accomplished by forming a salt of the racemic mixture with an optically active base such as (+) or (−) amphetamine, (−) cinchonidine, dehydroabietylamine, (+) or (−)-α-methylbenzylamine, (+) or (−)-α-(1-naphthyl)ethylamine, (+) cinchonine, brucine, or strychnine and the like in a suitable solvent such as methanol, ethanol, 2-propanol, benzene, acetonitrile, nitromethane, acetone and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer of the [(5,6,9-a-substituted-3-oxo-1,2,9,9-a-tetrahydro-3H-fluoren-7-yl)oxy]alkanoic a cycloalkanoic acid is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α- methylbenzylamine is used for the isolation of the second (remaining) enantiomer.

The compounds of Formula I which are esters (i.e. compounds of Formula IC, where $R^3$ is lower alkyl, alkenyl, alkynyl, cycloalkyl, substituted alkyl, such as carboxyalkyl, alkoxycarbonylakyl, hydroxyalkyl, carboxycycloalkyl, dihydroxyalkyl, trihydroxyalkyl, oxoalkyl, diloweralkylaminoalkyl, heterocyclic-alkyl, aralkyl and aryl) can be prepared by a variety of methods including one or more of the following seven methods.

The first method involves the etherification of compounds of Formula IV with a haloalkanoic acid ester or halocycloalkanoic acid ester such as X-A-COOR³, where X is halo and A is defined previously to produce compounds of Formula IC. The reaction is illustrated graphically below:

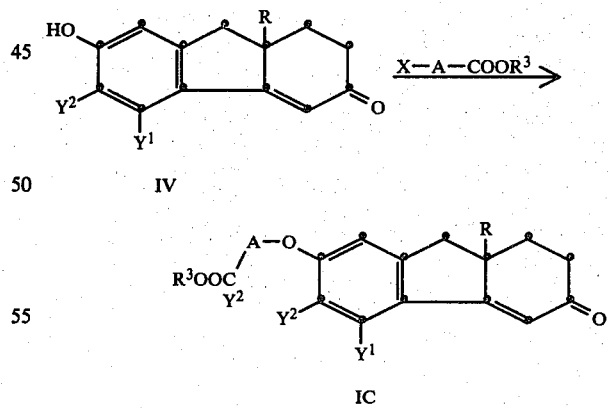

In general, the reaction is conducted in the presence of a base, such as an alkali metal carbonate, hydroxide or alkoxide such as potassium carbonate, sodium carbonate, potassium hydroxide, sodium ethoxide and the like. Solvents which are essentially inert to the reactants and product and in which the reactants and product are reasonably soluble are usually employed. Dimethylformamide, ethanol and acetone, for example, have been found to be especialy advantageous to use as solvents. The reaction may be conducted at a temperature in the range from about 25° C. to the boiling point temperature of the particular solvent employed. The reaction is generally complete in about 15 to 60 minutes; but, if lower temperatures are employed or if the particular halo ester is not very reactive, the reaction time may be much longer.

The second method for the synthesis of compounds of Formula IC involves the cyclization of compounds of Formula X to produce those of Formula IC. This method will be discussed later.

The third method for the preparation of compounds of Formula IC involves the esterification of compounds of Formula II. This may be accomplished by well known esterification methods such as those described for the conversion of compounds of Formula VIII to those of Formula IX (vide infra).

A fourth method involves a transesterification process as shown below.

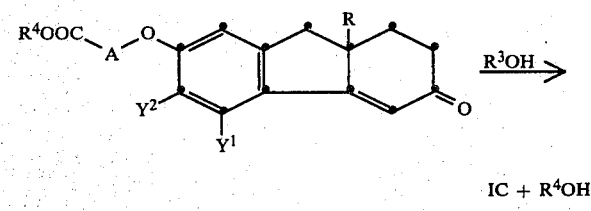

IC + R⁴OH

This involves heating an ester of Formula ID (where R⁴ is selected from the same group as R³ except it cannot be identical to R³ in this reaction). The reaction proceeds successfully with a variety of alcohols (R³OH) and is generally carried out in the presence of a catalytic amount of R³OM where M is a sodium or potassium ion. The reaction is carried out in the presence of an ion-exchange resin, such as, amberlite and the like. Solvents, such as, methylene chloride, chloroform, carbon tetrachloride, are employed and the reaction is conducted at temperatures ranging from 30° C. to the boiling point of the solvent employed. The reaction time varies from 2 hours to one day.

A fifth method consists of the esterification of a salt of the corresponding carboxylic acid (II) with the appropriate alkyl or aralkyl halide (R³X) where X represents halogen.

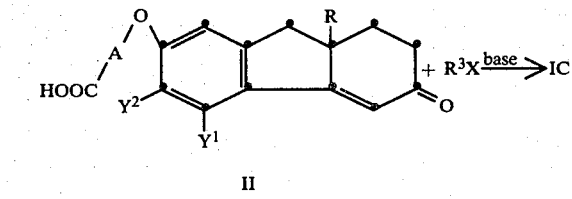

II

The reaction is carried out in the presence of a base, such as, potassium carbonate, sodium carbonate and the like which generates the corresponding salt of the compound of Formula II. The reaction is generally carried out in the presence of a solvent such as, dimethylformamide, dimethylacetamide, N-methylpyrrolidinone and the like at temperatures usually in the range of 50° to 120° C. The reaction time varies from one to 24 hours depending on the temperature and the nature of the reactants.

A sixth method consists of the reaction of a mixed anhydride of Formula XIX with an appropriate alcohol R³OH.

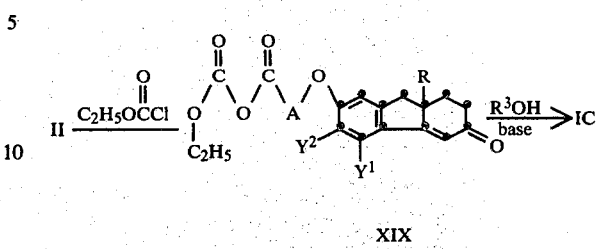

XIX

The mixed anhydride is generally generated in situ from the corresponding carboxylic acid (Formula II) and ethyl chloroformate in tetrahydrofuran (or similar solvent) at a low temperature (such as, −10° C. to +10° C.) in the presence of an appropriate base (such as triethylamine and the like). The alcohol, R³OH, is added and the reaction mixture gradually increased to ambient temperature over a period of one to 5 hours and finally heated at 50° C. to the boiling point of the solvent for one to 6 hours.

The seventh method involves the reaction of a 1-acylimidazole derivative of Formula XX with an alcohol of Formula R³OH.

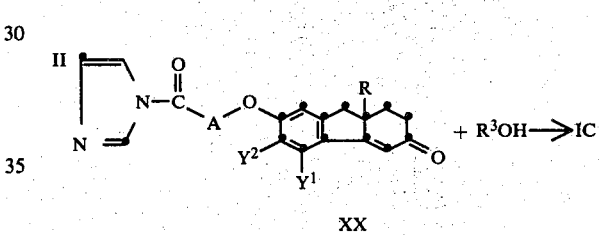

XX

The acylimidazole (XX) is generally prepared in situ by the reaction of a Compound II with 1,1'-carbonyldiimidazole in a solvent (such as tetrahydrofuran, 1,4-dioxane and the like) at a temperature of −10° to +10° C. Reaction of the alcohol (R³OH) with XX is generally conducted in the presence of a catalytic amount of a base (such as sodium hydride, KOC(CH₃)₃ and the like). The reaction is generally carried out at temperatures between 0° C. and ambient temperature and requires from one to 24 hours for completion.

It should be pointed out that the R³ moiety of the esters of Formula IC may possess a chemically reactive function which requires the presence of a chemical protective group during one or another of the seven synthetic methods described. These protective groups may be removed by one of several processes, such as selective hydrolysis, hydrogenolysis and the like.

The preparation of derivatives of the carboxylic acids (Formula II) of the invention are accomplished by methods well known by those skilled in the art. For example, an anhydride of Formula XXI is prepared from a compound of Formula II by reaction with a carbodiimide in an organic solvent. For example,

A

II + Carbodiimide 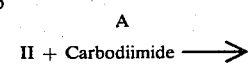

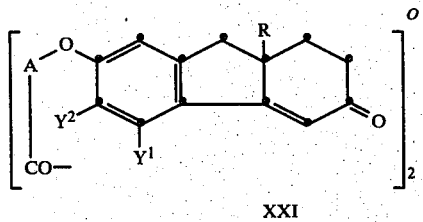

XXI a compound of Formula II can be reacted with a carbodiimide, sucb as N,N'-dicyclohexylcarbodiimide or N,N'-di-p-tolycarbodiimide in a solvent such as benzene, chlorobenzene, methylene chloride or dimethylformamide to produce a compound of Formula XXI.

The amide, hydrazide, guanidide and the like derivatives (Formula XXII) of compounds of the invention are prepared by methods well known to those skilled in the art. For example, a compound of Formula II is converted to the acylimidazole (XX) (described above) which, in turn, is treated

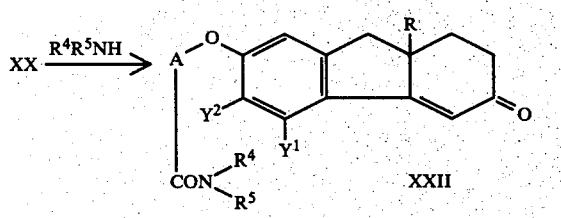

XXII with the appropriate base ($R^4R^5NH$) to obtain the desired derivative (Formula XXII). Thus, if $R^4R^5NH$ represents ammonia or an amine, i.e., where $R^4$ and $R^5$ are hydrogen or lower alkyl, and the like, the product is an amide. If $R^4R^5NH$ represents a hydrazide, i.e., $R^4$ is amino or dilower-alkylamino and $R^5$ is hydrogen or lower alkyl, the product is a hydrazide. If $R^4$ is

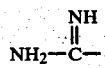

and $R^5$ is hydrogen the product is quanidide.

The reactions described may be conducted in an excess of the reactant base as a solvent or one may use a conventional solvent, such as dimethylformamide, 1-methylpyrrolidin-2-one and the like.

The acid addition salts of Formula XXIII (where B+ represents a cation from a pharmaceutically acceptable base) are prepared by reacting a carboxylic acid of Formula II with an appropriate alkali metal or alkaline earth bicarbonate, carbonate or alkoxide, an amine, ammonia, an organic quaternary ammonium hydroxide, guanidine and the like. The reaction is illustrated below:

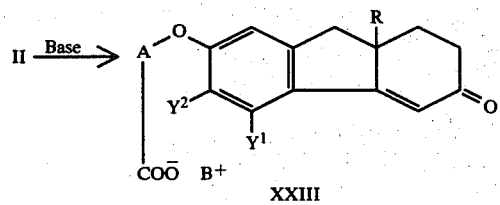

XXIII

The reaction is generally conducted in water but when alkali metal hydroxides and alkoxides and the organic bases are used, the reaction may be conducted in an organic solvent, such as ethanol, dimethylformamide and the like.

The preferred salts are the sodium, ammonium, diethanolamine, 1-methylpiperazine, piperazine and the like salts.

Inasmuch as there is a wide variety of symptoms and severity associated with grey matter edema, particularly when it is caused by blows to the head or spinal chord, the precise treatment protocol is left to the practitioner. It is up to the practitioner to determine the patient's response to treatment and to vary the dosages accordingly. A recommended dosage range is from 1 μg. to 10 mg./kg of body weight as a primary dose and a sustaining dose of half to equal the primary dose, every 4 to 24 hours.

The compounds of this invention can be administered by a variety of established methods, including intravenously, intramuscularly, subcutaneously, and orally. As with dosage, the precise mode of administration is left to the discretion of the practitioner.

Recent studies in experimental head injury by R. S. Bourke et al. (R. S. Bourke, M. A. Daze and H. K. Kimelberg, Monograph of the International Glial Cell Symposium, Leige, Bel. Aug. 29–31, 1977 and references cited therein) and experimental stroke by J. H. Garcia et al. (J. H. Garcia, H. Kalimo, Y. Kamijyo and B. F. Trump, Virchows Archiv. [Zellopath.], 25, 191 (1977), indicate that astroglial swelling, a secondary and potentially inhibitable process, is a fundamental pathophysilogical response to ischemic/traumatic brain insult in both pathological disorders. Furthermore, astroglial swelling is believed to reduce oxygen available to neurons by prolongation of the oxygen diffusion pathaway. Thus, the damage to cerebral grey matter may be far more extensive as a result of pathological events secondary to astroglial swelling than as a result of damage inflicted by the initial ischemic/traumatic insult. Consequently, it is of prime importance that the treatment commence as soon as possible after the initial trauma in order to minimize the brain cell damage and the possibility of death or permanent paralysis.

One aspect of this invention is the treatment of persons with grey matter edema by concomitant administration of a compound of formula I, IC or II or a pharmaceutically acceptable salt, or amide thereof and an antiinflammatory steroid. These steroids are of some albeit limited, use in control of white matter edema associated with ischemic stroke and head injury. Steroid therapy is given according to established practice as a supplement to the compound of formula I, IC or II as taught elsewhere herein.

The compounds of formula I, IC or II are utilized by formulating them in a composition such as tablet, capsule or elixir for oral adminstration. Sterile solutions or suspensions can be used for parenteral administration. About 70 μg to 750 mg. of a compound or mixture of compounds of formulae I, IC, or II of a physiologically acceptable salt, or amide is compounded with a physiologically acceptable vehicle, carrier, excipient, binder, preservative, stabilizer, flavor, etc. in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are included to illustrate the preparation of representative dosage forms.

EXAMPLE 1

[(5,6-Dichloro-9a-ethyl-3-oxo-1,2,9,9a-tetrahydro-3H-fluoren-7yl)oxy]acetic Acid Steps A and B. 5,6-Dichloro-9a-ethyl-7-methoxy-1,2,9,9a-tetrahydro-3H-fluoren-3-one 6,7-Dichloro-2-ethyl-5-methoxy-2,3-dihydro-1H-inden-1-one (32.4 gm., 0.125 mole) is dissolved in tetrahydrofuran (300 ml.) and 40% triton-B in methanol (3ml.) is added. Methyl vinyl ketone (12.3 gm., 0.175 moles) is added dropwise to the stirring reaction mixture over a period of 10 minutes. The temperature rises from 26° C. to 35° C. The mixture is stirred for an additional hour and most of the volatile material is removed by evaporation in vacuo using a rotary evaporator.

Water (200 ml.) is added and the mixture extracted with ether (three 100 ml. portions). The combined ether extracts are dried over $Na_2SO_4$ and then evaporated in vacuo to give a residual oil which is 6,7-dichloro-2-ethyl-5-methoxy-2-(3-oxobutyl)-2,3-dihydro-1H-inden-1-one. This material is dissolved in dry benzene (200 ml.), placed in a constant water separator (Dean-Stark), treated with acetic acid (1.5 ml.) and pyrrolidine (1.5 ml.). The mixture is refluxed for two hours after which time water ceases to separate. Then the solvent is distilled until only 50 ml. remains and then methanol (100 ml.) is added. Upon chilling in an ice bath, 5,6-dichloro-9a-ethyl-7-methoxy-1,2,9,9a-tetrahydro-3H-fluoren-3-one (16.2 gm.) separates, m.p. 159°-165° C. This material is satisfactory for use in the next step.

Step C. 5,6-Dichloro-9a-ethyl-7-hydroxy-1,2,9,9a-tetrahydro-3H-fluoren-3-one.

5,6-Dichloro-9a-ethyl-7-methoxy-1,2,9,9a-tetrahydro-3H-fluoren-3-one (15 gm., 0.048 mole) is mixed with pyridine hydrochloride (120 gm.) in a reaction vessel and heated in a metal bath at 195°-200° C. for 30 minutes. The mixture is cooled somewhat and poured with stirring into cold water (800 ml.). The solid that separates is removed by filtration and washed with water. After drying, the product is triturated with acetonitrile (80 ml.) at 60°, cooled, filtered and dried. The yield of crude 5,6-dichloro-9a-ethyl-7-hydroxy-1,2,9,9a-tetrahydro-3H-fluoren-3-one is 12.2 gm., m.p. 260°-265° C. This material is pure enough for use in the next step.

Step D. Ethyl [(5,6-Dichloro-9a-ethyl-3-oxo-1,2,9,9a-tetrahydro-3H-fluoren-7-yl)oxy]acetate A mixture of 5,6-dichloro-9a-ethyl-7-hydroxy-1,2,9,9a-tetrahydro-3H-fluoren-3-one (6.0 gm., 0.02 mole), ethyl bromoacetate (4.0 gm., 0.025 mole) and potassium carbonate (8.3 gm., 0.06 mole) in dimethylformamide (35 ml.) is heated at 50° C. and stirred for one hour. The mixture is cooled and poured into water (300 ml.). The solid product that separates is removed by filtration, then washed with water followed by benzene (10 ml.).

The yield of ethyl [(5,6-dichloro-9a-ethyl-3-oxo-1,2,9,9a-tetrahydro-3H-fluoren-7-yl)oxy]acetate after drying, is 6.9 gm. After two recrystallizations from acetonitrile 4.8 gm. remains, m.p. 164°-166° C.

Step E. [(5,6-Dichloro-9a-ethyl-3-oxo-1,2,9,9a-tetrahydro-3H-fluoren-7-yl)oxy]acetic Acid Ethyl [(5,6-dichloro-9a-ethyl-3-oxo-1,2,9,9a-tetrahydro-3H-fluoren-7-yl)oxy]acetate (4.8 gm., 0.012 mole) is dissolved in acetic acid (30 ml.) containing 5% aqueous hydrochloride acid (10 ml.). The mixture is heated and stirred on a stream bath for an hour. The solution is diluted with water (8 ml.) and cooled. The product that separates is recrystallized twice from a 1:6 (v/v) mixture of water and acetic acid. The yield of [(5,6-dichloro-9a-ethyl-3-oxo-1,2,9,9a-tetrahydro-3H-fluoren-7-yl)-oxy]acetic acid is 2.6 gm., m.p. 237°-238° C.

Anal. Calcd. for $C_{17}H_{16}Cl_2O_4$: C, 57.48; H, 4.54. Found: C, 57.97; H, 4.43. C, 57.21; H, 4.29.

Using a procedure similar to that described in Example 1, except in Step A there is substituted for the 6,7-dichloro-2-ethyl-5-methoxy-2,3-dihydro-1H-inden-1-one an equimolar amount of:

EXAMPLE 2

Step A. 6,7-Dichloro-5-methoxy-2,3-dihydro-1H-inden-1-one.

EXAMPLE 3

Step A. 6,7-Dichloro-5-methoxy-2-methyl-2,3-dihydro-1H-inden-1-one.

EXAMPLE 4

Step A. 6,7-Dichloro-5-methoxy-2-propyl-2,3-dihydro-1H-inden-1-one.

EXAMPLE 5

Step A. 6,7-Dichloro-2-isopropyl-5-methoxy-2,3-dihydro-1H-inden-1-one.

EXAMPLE 6

Step A. 2-Butyl-6,7-dichloro-5-methoxy-2,3-dihydro-1H-inden-1-one.

EXAMPLE 7

Step A. 6,7-Dichloro-2-isobutyl-5-methoxy-2,3-dihydro-1H-inden-1-one.

EXAMPLE 8

Step A. 6,7-Dichloro-2-cyclopentyl-5-methoxy-2,3-dihydro-1H-inden-1-one.

EXAMPLE 9

Step A. 2-Benzyl-6,7-dichloro-5-methoxy-2,3-dihydro-1H-inden-1-one.

EXAMPLE 10

Step A. 6,7-Dichloro-5-methoxy-2-phenyl-2,3-dihydro-1H-inden-1-one.

In Examples 2, Step A through Example 10, Step A, the reaction is carried out as described in Example 1, Step A, then by using each product and conducting the reaction as in Example 1, Step B, there is obtained:

EXAMPLE 2

Steps A and B: 6,7-Dichloro-5-methoxy-2-(3-oxobutyl)-2,3-dihydro-1H-inden-1-one and then 5,6-dichloro-7-methoxy-1,2,9,9a-tetrahydro-3H-fluoren-3-one.

EXAMPLE 3

Steps A and B. 6,7-Dichloro-5-methoxy-2-methyl-2-(3-oxobutyl)-2,3-dihydro-1H-inden-1-one and then 5,6-dichloro-7-methoxy-9a-methyl-1,2,9,9a-tetrahydro-3H-fluoren-3-one.

EXAMPLE 4

Steps A and B. 6,7-Dichloro-5-methoxy-2-(3-oxobutyl)-2-propyl-2,3-dihydro-1H-inden-1-one and then 5,6-dichloro-7-methoxy-9a-propyl-1,2,9,9a-tetrahydro-3H-fluoren-3-one.

EXAMPLE 5

Steps A and B. 6,7-Dichloro-2-isopropyl-5-methoxy-2-(3-oxobutyl)-2,3-dihydro-1H-inden-1-one and then 5,6-dichloro-9a-isopropyl-7-methoxy-1,2,9,9a-tetrahydro-3H-fluoren-3-one.

EXAMPLE 6

Steps A and B. 2-Butyl-6,7-dichloro-5-methoxy-2-(3-oxobutyl)-2,3-dihydro-1H-inden-1-one and then 9a-butyl-5,6-dichloro-7-methoxy-1,2,9,9a-tetrahydro-3H-fluoren one.

EXAMPLE 7

Steps A and B. 6,7-Dichloro-2-isobutyl-5-methoxy-2-(3-oxobutyl)-2,3-dihydro-1H-inden-1-one and then 5,6-dichloro-9a-isobutyl-7-methoxy-1,2,9,9a-tetrahydro-3H-fluoren-3-one.

EXAMPLE 8

Steps A and B. 6,7-Dichloro-2-cyclopentyl-5-methoxy-2-(3-oxobutyl)-2,3-dihydro-1H-inden-1-one and then 5,6-dichloro-9a-cyclopentyl-7-methoxy-1,2,9,9a-tetrahydro-3H-fluoren-3-one.

EXAMPLE 9

Steps A and B. 2-Benzyl-6,7-dichloro-5-methoxy-2-(3-oxobutyl)-2,3-dihydro-1H-inden-1-one and then 9a-benzyl-5,6-dichloro-7-methoxy-1,2,9,9a-tetrahydro-3H-fluoren-3-one.

EXAMPLE 10

Steps A and B. 6,7-Dichloro-5-methoxy-2-(3-oxobutyl)-2-phenyl-2,3-dihydro-1H-inden-1-one and then 5,6-dichloro-7-methoxy-9a-phenyl-1,2,9,9a-tetrahydro-3H-fluoren-3-one.

Carrying out the reaction as described in Example 1, Step C, except that the 5,6-dichloro-7-methoxy-1,2,9,9a-tetrahydro-3H-fluoren-3-one of Example 1, Step C is substituted by an equimolar quantity of the product of Example 2, Step B, Example 3, Step B, Example 4, Step B, Example 5, Step B, Example 6, Step B, Example 7, Step B, Example 8, Step B, Example 9, Step B, and Example 10, Step B to obtain:

EXAMPLE 2

Step C. 5,6-Dichloro-7-hydroxy-1,2,9,9a-tetrahydro-3H-fluoren-3-one.

EXAMPLE 3

Step C. 5,6-Dichloro-7-hydroxy-9a-methyl-1,2,9,9a-tetrahydro-3H-fluoren-3-one.

EXAMPLE 4

Step C. 5,6-Dichloro-7-hydroxy-9a-propyl-1,2,9,9a-tetrahydro-3H-fluoren-3-one.

EXAMPLE 5

Step C. 5,6-Dichloro-7-hydroxy-9a-isopropyl-1,2,9,9a-tetrahydro-3H-fluoren-3-one.

EXAMPLE 6

Step C. 9a-Butyl-5,6-dichloro-7-hydroxy-1,2,9,9a-tetrahydro-3H-fluoren-3-one.

EXAMPLE 7

Step C. 5,6-Dichloro-9a-isobutyl-7-hydroxy-1,2,9,9a-tetrahydro-3H-fluoren-3-one.

EXAMPLE 8

Step C. 5,6-Dichloro-9a-cyclopentyl-7-hydroxy-1,2,9,9a-tetrahydro-3H-fluoren-3-one.

EXAMPLE 9

Step C. 9a-Benzyl-5,6-dichloro-7-hydroxy-1,2,9,9a-tetrahydro-3-fluoren-3-one.

EXAMPLE 10

Step C. 5,6-Dichloro-7-hydroxy-9a-phenyl-1,2,9,9a-tetrahydro-3H-fluoren-3-one.

Carrying out the reaction as described in Example 1, Step D, except that the 5,6-dichloro-9a-ethyl-7-hydroxy-1,2,9,9a-tetrahydro-3H-fluoren-3-one of Example 1, Step D, is substituted by an equimolar quantity of the product of Example 2, Step C, Example 3, Step C, Example 4, Step C, Example 5, Step C, Example 6, Step C, Example 7, Step C, Example 8, Step C, Example 9, Step C or Example 10, Step C to obtain:

EXAMPLE 2

Step D. Ethyl [(5,6-dichloro-3-oxo-1,2,9,9a-tetrahydro-3H-fluoren-7-yl)oxy]acetate.

EXAMPLE 3

Step D. Ethyl [(5,6-dichloro-9a-methyl-3-oxo-1,2,9,9a-tetrahydro-3H-fluoren-7-yl)oxy]acetate.

EXAMPLE 4

Step D. Ethyl [(5,6-dichloro-3-oxo-9a-propyl-1,2,9,9a-tetrahydro-3H-fluoren-7-yl)oxy]acetate.

EXAMPLE 5

Step D. Ethyl [(5,6-dichloro-9a-isopropyl-3-oxo-1,2,9,9a-tetrahydro-3H-fluoren-7-yl)oxy]acetate.

EXAMPLE 6

Step D. Ethyl [(9a-butyl-5,6-dichloro-3-oxo-1,2,9,9a-tetrahydro-3H-fluoren-7-yl)oxy]acetate.

EXAMPLE 7

Step D. Ethyl [(5,6-dichloro-9a-isobutyl-3-oxo-1,2,9,9a-tetrahydro-3H-fluoren-7-yl)oxy]acetate.

EXAMPLE 8

Step D. Ethyl [(5,6-dichloro-9a-cyclopentyl-3-oxo-1,2,9,9a-tetrahydro-3H-fluoren-7-yl)oxy]acetate.

EXAMPLE 9

Step D. Ethyl [(9a-benzyl-5,6-dichloro-3-oxo-1,2,9,9a-tetrahydro-3H-fluoren-7-yl)oxy]acetate.

EXAMPLE 10

Step D. Ethyl [(5,6-dichloro-3-oxo-9a-phenyl-1,2,9,9a-tetrahydro-3H-fluoren-7-yl)oxy]acetate.

Carrying out the reaction as described in Example 1, Step E, except that the ethyl [(5,6-dichloro-9a-ethyl-3-oxo-1,2,9,9a-tetrahydro-3H-fluoren-7-yl)oxy]acetate of Example 1, Step E is substituted by an equimolar quantity of the product of Example 2, Step D, Example 3, Step D, Example 4, Step D, Example 5, Step D, Example 6, Step D, Example 7, Step D, Example 8, Step D, Example 9, Step D or Example 10, whereby there is obtained:

EXAMPLE 2

Step E. [(5,6-Dichloro-3-oxo-1,2,9,9a-tetrahydro-3H-fluoren-7-yl)oxy]acetic acid.

EXAMPLE 3

Step E. [(5,6-Dichloro-9a-methyl-3-oxo-1,2,9,9a-tetrahydro-3H-fluoren-7-yl)oxy]acetic acid.

EXAMPLE 4

Step E. [(5,6-Dichloro-3-oxo-9a-propyl-1,2,9,9a-tetrahydro-3H-fluoren-7-yl)oxy]acetic acid.

EXAMPLE 5

Step E. [(5,6-Dichloro-3-oxo-9a-isopropyl-1,2,9,9a-tetrahydro-3H-fluoren-7-yl)oxy]acetic acid.

EXAMPLE 6

Step E. [(9a-Butyl-5,6-dichloro-3-oxo-1,2,9,9a-tetrahydro-3H-fluoren-7-yl)oxy]acetic acid.

EXAMPLE 7

Step E. [(5,6-Dichloro-9a-isobutyl-3-oxo-1,2,9,9a-tetrahydro-3H-fluoren-7-yl)oxy]acetic acid.

EXAMPLE 8

Step E. [(5,6-Dichloro-9a-cyclopentyl-3-oxo-1,2,9,9a-tetrahydro-3H-fluoren-7-yl)oxy]acetic acid.

EXAMPLE 9

Step E. [(9a-Benzyl-5,6-dichloro-3-oxo-1,2,9,9a-tetrahydro-3H-fluoren-7-yl)oxy]acetic acid.

EXAMPLE 10

Step E. [(5,6-Dichloro-3-oxo-9a-phenyl-1,2,9,9a-tetrahydro-3H-fluoren-7-yl)oxy]acetic acid.

By carrying out the reaction as described in Example 1, Step D, except that the ethyl bromoacetate is substituted by an equimolar quantity of:

EXAMPLE 11

Step A. Ethyl 2-bromopropanoate.

EXAMPLE 12

Step A. Ethyl 2-bromobutyrate.

EXAMPLE 13

Step A. Ethyl 2-bromo-2-methylpropanoate.

EXAMPLE 14

Step A. Ethyl 1-bromocyclobutane-1-carboxylate.
There is obtained:

EXAMPLE 11

Step A. Ethyl 2-[(5,6-dichloro-9a-ethyl-3-oxo-1,2,9,9a-tetrahydro-3H-fluoren-7-yl)oxy]propanoate.

EXAMPLE 12

Step A. Ethyl 2-[(5,6-dichloro-9a-ethyl-3-oxo-1,2,9,9a-tetrahydro-3H-fluoren-7-yl)oxy]butyrate.

EXAMPLE 13

Step A. Ethyl 2-methyl-2-[(5,6-dichloro-9a-ethyl-3-oxo-1,2,9,9a-tetrahydro-3H-fluoren-7-yl)oxy]propanoate.

EXAMPLE 14

Step A. Ethyl 1-[(5,6-dichloro-9a-ethyl-3-oxo-1,2,9,9a-tetrahydro-3H-fluoren-7-yl)oxy]cyclobutane-1-carboxylate.

By carrying out the reaction as described in Example 1, Step D, except that the 5,6-dichloro-9a-ethyl-7-hydroxy-1,2,9,9a-tetrahydro-3H-fluoren-3-one is substituted by 5,6-dichloro-7-hydroxy-9a-methyl-1,2,9,9a-tetrahydro-3H-fluoren-3-one (Example 3, Step C) and the ethyl bromoacetate subtituted by Example 15, Step A: ethyl 2-bromo-2-methylpropanoate Example 16, Step A: ethyl 1-bromocyclobutane-1-carboxylate. There is obtained:

EXAMPLE 15

Step A. Ethyl 2-methyl-2-[(5,6-dichloro-9a-methyl-3-oxo-1,2,9,9a-tetrahydro-3H-fluoren-7-yl)oxy]propanoate.

EXAMPLE 16

Step A. Ethyl 1-[(5,6-dichloro-9a-methyl-3-oxo-1,2,9,9a-tetrahydro-3H-fluoren-7-yl)oxy]cyclobutane-1-carboxylate.

By carrying out the reaction as described in Example 1, Step E, except that the ethyl [(5,6-dichloro-9a-ethyl-3-oxo-1,2,9,9a-tetrahydro-3H-fluoren-7-yl)oxy]acetate is substituted by the product of Example 11, Step A, Example 12, Step A, Example 13, Step A, Example 14, Step A, Example 15, Step A, or Example 16, Step A, whereby there is obtained:

EXAMPLE 11

Step B. 2-[(5,6-Dichloro-9a-ethyl-3-oxo-1,2,9,9a-tetrahydro-3H-fluoren-7-yl)oxy]propanoic acid.

EXAMPLE 12

Step B. 2-[(5,6-Dichloro-9a-ethyl-3-oxo-1,2,9,9a-tetrahydro-3H-fluoren-7-yl)oxy]butyric acid.

EXAMPLE 13

Step B. 2-Methyl-2-[(5,6-dichloro-9a-ethyl-3-oxo-1,2,9,9a-tetrahydro-3H-fluoren-7-yl)oxy]propanoic acid.

EXAMPLE 14

Step B. 1-[(5,6-Dichloro-9a-ethyl-3-oxo-1,2,9,9a-tetrahydro-3H-fluoren-7-yl)oxy]cyclobutane-1-carboxylic acid.

EXAMPLE 15

Step B. 2-Methyl-2-[(5,6-dichloro-9a-methyl-3-oxo-1,2,9,9a-tetrahydro-3H-fluoren-7-yl)oxy]propanoic acid.

EXAMPLE 16

Step B. 1-[(5,6-Dichloro-9a-methyl-3-oxo-1,2,9,9a-tetrahydro-3H-fluoren-7-yl)oxy]cyclobutane-1-carboxylic acid.

EXAMPLE 17

3-[(5,6-Dichloro-9a-methyl-3-oxo-1,2,9,9a-tetrahydro-3H-fluoren-7-yl)oxy]propanoic acid 5,6-Dichloro-7-hydroxy-9a-methyl-1,2,9,9a-tetrahydro-3H-fluoren-3-one (9.0 gm., 0.03 mole) is dissolved in 10% aqueous sodium hydroxide solution (35 ml.). The solution is heated to boiling with stirring, the heat source is removed and β-propiolactone (23.8 gm., 0.33 mole) is added at such a rate to keep the solution boiling. During the reaction, 10% aqueous sodium hydroxide is added as necessary to keep the reaction mixture alkaline to litmus paper.

When the reaction is complete, the solution is cooled and made acid to Congo red paper with 6 normal hydrochloric acid. The product that separates is removed by filtration and dissolved by treatment with a 5% solution of sodium hydroxide (three 50 ml. portions). The combined aqueous extracts are acidified to Congo red paper with 6 normal hydrochloric acid. The product is removed by filtration, washed with water and dried. Recrystallization from a mixture of acetic acid and water gives pure 3-[(5,6-dichloro-9a-methyl-3-oxo-1,2,9,9a-tetrahydro-3H-fluoren-7-yl)oxy]propanoic acid.

Carrying out the reaction as described in Example 17 except that the 5,6-dichloro-9a-methyl-7-hydroxy-1,2,9,9a-tetrahydro-3H-fluoren-3-one is substituted by an equimolar quantity of:

EXAMPLE 18

5,6-Dichloro-9a-ethyl-7-hydroxy-1,2,9,9a-tetrahydro-3H-fluoren-3-one.

EXAMPLE 19

5,6-Dichloro-7-hydroxy-9a-isopropyl-1,2,9,9a-tetrahydro-3H-fluoren-3-one. There is obtained:

EXAMPLE 18

3-[(5,6-Dichloro-9a-ethyl-3-oxo-1,2,9,9a-tetrahydro-3H-fluoren-7-yl)oxy]propanoic acid.

EXAMPLE 19

3-[(5,6-Dichloro-9a-isopropyl-3-oxo-1,2,9,9a-tetrahydro-3H-fluoren-7-yl)oxy]propanoic acid.

EXAMPLE 20

[(5,6-Dichloro-9a-ethyl-3-oxo-1,2,9,9a-tetrahydro-3H-fluoren-7-yl)oxy]acetic acid Step A. Methyl [(6,7-dichloro-2-ethyl-1-oxo-2,3-dihydro-1H-inden-5-yl)oxy]acetate

[(6,7-Dichloro-2-ethyl-1-oxo-2,3-dihydro-1H-inden-5-yl)oxy]acetic acid (31.7 gm. 0.1 mole) is dissolved in dimethylformamide (300 ml.) and potassium carbonate (20.7 gm., 0.15 mole) is added. The mixture is stirred and heated at 60° C. for 10 minutes in a vessel protected from atmospheric moisture. Methyl iodide (12.6 ml., 28.4 gm., 0.2 mole) is added and heating and stirring continued for 3 hours. The mixture is cooled, added, with stirring to water (3 liters) and the solid that separated removed by filtration and dried. Recrystallization from methanol gives 27 gm. of methyl [(6,7-dichloro-2-ethyl-1-oxo-2,3-dihydro-1H-inden-5-yl)oxy]acetate.

Step B. Methyl{[6,7-dichloro-2-ethyl-1-oxo-2-(3-oxobutyl)-2,3-dihydro-1H-inden-5-yl]oxy}acetate Methyl [(6,7-dichloro-2-ethyl-1-oxo-2,3-dihydro-1H-inden-5-yl)oxy]acetate (15.8 gm., 0.05 mole) is suspended in dry tetrahydrofuran (100 ml.) containing triton-B (1 ml.). The suspension is stirred at ambient temperature and methyl vinyl ketone (5.02 gm., 0.072 mole) is added. The solution which becomes warm initially, is stirred at ambient temperature for 4 hours. Then, the stirring solution is treated with methyl vinyl ketone (0.3 ml.) and triton-B (0.6 ml.) every 4 hours for the next twenty hours.

The reaction mixture is evaporated in vacuo at 50° C. and the residual material dissolved in ether (100 ml.). The ether solution is washed with water (two 20 ml. portions), dried over anhydrous magnesium sulfate and filtered. The filtrate is evaporated in vacuo and the residue triturated with ether (10 ml.), filtered and dried. The yield of methyl {[6,7-dichloro-2-ethyl-1-oxo-2-(3-oxobutyl)-2,3-dihydro-1H-inden-5-yl]oxy}acetate is 12.3 gm., m.p. 78°–79° C. This material is adequate for use in the next step.

Step C. Methyl [(5,6-dichloro-9a-ethyl-3-oxo-1,2,9,9a-tetrahydro-3H-fluoren-7-yl)oxy]acetate A mixture of methyl {[6,7-dichloro-2-ethyl-1-oxo-2-(3-oxobutyl)-2,3-dihydro-1H-inden-5-yl]oxy}acetate (9.0 gm., 0.024 mole), pyrrolidine (1.70 gm., 0.024 mole) and acetic acid (1.42 gm., 0.024 mole) in toluene (100 ml.) is heated at 85° C. for one hour. The solution is concentrated in vacuo at 50° C. to obtain the crude product.

The product is subjected to column chromatography on silica gel (300 gm.) using a mixture of dichloromethane and tetrahydrofuran (100/4 v./v.) as the eluent. The yield of pure methyl [(5,6-dichloro-9a-ethyl-3-oxo-1,2,9,9a-tetrahydro-3H-fluoren-7-yl)oxy]acetate is 5.05 gm., m.p. 182°–183° C.

Step D. [(5,6-Dichloro-9a-ethyl-3-oxo-1,2,9,9a-tetrahydro-3H-fluoren-7-yl)oxy]acetic acid Methyl [(5,6-dichloro-9a-ethyl-3-oxo-1,2,9,9a-tetrahydro-3H-fluoren-7-yl)oxy]acetate (4.0 gm., 0.011 mole) is added to a solution composed of 20% aqueous sodium hydroxide solution (4.32 ml., 0.022 mole) and methanol (45 ml.). The mixture is stirred and heated at reflux for two hours and then concentrated in vacuo at 50° C. The residue is dissolved in water (50 ml.) and made acid to Congo red paper with 6 normal hydrochloric acid. The solid that separates is removed by filtration, washed with water, then with a little methanol and finally with a little ether. After drying, the product weighs 3.14 gm., m.p. 235° C. After recrystallization from acetic acid, the yield of pure [(5,6-dichloro-9a-ethyl-3-oxo-1,2,9,9a-tetrahydro-3H-fluoren-7-yl)oxy]acetic acid is 2.61 gm., m.p. 237°–239° C.

Anal. Calcd. for $C_{17}H_{16}Cl_2O_4$: C, 57.48; H, 4.54. Found: C, 57.35; H, 4.62.

Carrying out the reaction as described in Example 20, Step A, except that the [(6,7-dichloro-2-ethyl-1-oxo-2,3-dihydro-1H-inden-5-yl)oxy]acetic acid is substituted by an equimolar quantity of:

EXAMPLE 21

Step A. [(6,7-Dichloro-1-oxo-2-propyl-2,3-dihydro-1H-inden-5-yl)oxy]acetic acid.

EXAMPLE 22

Step A. [(2-Butyl-6,7-dichloro-1-oxo-2,3-dihydro-1H-inden-5-yl)oxy]acetic acid.

EXAMPLE 23

Step A. [(2-Ethyl-6,7-dimethyl-1-oxo-2,3-dihydro-1H-inden-5-yl)oxy]acetic acid.

EXAMPLE 24

Step A. [(2-Ethyl-1-oxo-2,3-dihydro-1H-benz[e]inden-5-yl)oxy]acetic acid. There is obtained:

EXAMPLE 21

Step A. Methyl [(6,7-dichloro-1-oxo-2-propyl-2,3-dihydro-1H-inden-5-yl)oxy]acetate.

EXAMPLE 22

Step A. Methyl [(2-Butyl-6,7-dichloro-1-oxo-2,3-dihydro-1H-inden-5-yl)oxy]acetate.

EXAMPLE 23

Step A. Methyl [(2-ethyl-6,7-dimethyl-1-oxo-2,3-dihydro-1H-inden-5-yl)oxy]acetate.

EXAMPLE 24

Step A. Methyl [(2-ethyl-1-oxo-2,3-dihydro-1H-benz[e]inden-5-yl)oxy]acetate.

Carrying out the reaction as described in Example 20, Step B, except that the methyl [(6,7-dichloro-2-ethyl-1-oxo-2,3-dihydro-1H-inden-5-yl)-oxy]acetate is substituted by an equimolar quantity of the product of Example 21, Step A, Example 22, Step A, Example 23, Step A or Example 24, Step A. There is obtained:

EXAMPLE 21

Step B. Methyl {[6,7-dichloro-2-propyl-1-oxo-2-(3-oxobutyl)-2,3-dihydro-1H-inden-5-yl)]oxy}acetate, m.p. 91°–93° C.

EXAMPLE 22

Step B. Methyl {[6,7,dichloro-2-butyl-1-oxo-2-(3-oxobutyl)-2,3-dihydro-1H-inden-5-yl]oxy}acetate, m.p. 92°–93° C.

EXAMPLE 23

Step B. Methyl {[2-ethyl-6,7-dimethyl-1-oxo-2-(3-oxobutyl)-2,3-dihydro-1H-inden-5-yl]oxy}acetate.

EXAMPLE 24

Step B. Methyl {[2-ethyl-1-oxo-2-(3-oxobutyl)-2,3-dihydro-1H-benz[e]inden-5-yl]oxy}acetate.

Carrying out the reaction as described in Example 20, Step C, except that the methyl {[6,7-dichloro-2-ethyl-1-oxo-2-(3-oxobutyl)-2,3-dihydro-1H-inden-5-yl]oxy}acetate is substituted by an equimolar quantity of the product of Example 21, Step B, Example 22, Step B, Example 23, Step B, or Example 24, whereby there is obtained:

EXAMPLE 21

Step C. Methyl [(5,6-dichloro-3-oxo-9a-propyl-1,2,9,9a-tetrahydro-3H-fluoren-7-yl)oxy]acetate, m.p. 158°–159° C.

EXAMPLE 22

Step C. Methyl [(9a-butyl-5,6-dichloro-3-oxo-1,2,9,9a-tetrahydro-3H-fluoren-7-yl)oxy]acetate, 153.5°–154° C.

EXAMPLE 23

Step C. Methyl [(9a-ethyl-5,6-dimethyl-3-oxo-1,2,9,9a-tetrahydro-3H-fluoren-7-yl)oxy]acetate.

EXAMPLE 24

Step C. Methyl [(7a-ethyl-10-oxo-7,7a,8,9-tetrahydro-10H-benzo[c]fluoren-5-yl)oxy]acetate.

Carrying out the reaction as described in Example 20, Step D, except that the methyl [(5,6-dichloro-9a-ethyl-3-oxo-1,2,9,9a- tetrahydro-3H-fluoren-7-yl)oxy]acetate is substituted by an equimolar quantity of the product of Example 21, Step C, Example 22, Step C, Example 23, Step C or Example 24, Step C. There is obtained:

EXAMPLE 21

Step D. [(5,6-Dichloro-3-oxo-9a-propyl-1,2,9,9a-tetrahydro-3H-fluoren-7-yl)oxy]acetic acid.

EXAMPLE 22

Step D. [(9a-Butyl-5,6-dichloro-3-oxo-1,2,9,9a-tetrahydro-3H-fluoren-7-yl)oxy]acetic acid.

EXAMPLE 23

Step D. [(9a-Ethyl-5,6-dimethyl-3-oxo-1,2,9,9a-tetrahydro-3H-fluoren-7-yl)oxy]acetic acid.

EXAMPLE 24

Step D. [(7a-Ethyl-10-oxo-7,7a,8,9-tetrahydro-10H-benzo[c]fluoren-5-yl)oxy]acetic acid.

EXAMPLE 25

[(5,6-Dichloro-9a-isopropyl-3-oxo-1,2,9,9a-tetrahydro-3H-fluoren-7-yl)oxy]acetic acid Step A. Methyl [(6,7-dichloro-2-isopropyl-1-oxo-2,3-dihydro-1H-inden-5-yl)oxy]acetate

[(6,7-Dichloro-2-isopropyl-1-oxo-2,3-dihydro-1H-inden-5-yl)oxy]acetic acid 33.4 gm. 0.1 mole) is dissolved in dimethylformamide (300 ml.) and potassium carbonate (20.7 gm., 0.15 mole) is added. The mixture is stirred and heated at 60° C. for 10 minutes in a vessel protected from atmospheric moisture. Methyl iodide (12.6 ml., 28.4 gm., 0.2 mole) is added and heating and stirring continued for 3 hours. The mixture is cooled, added, with stirring to water (3 liters) and the solid that separated removed by filtration and dried. Recrystallization from methanol gives methyl [(6,7-dichloro-2-isopropyl-1-oxo-2,3-dihydro-1H-inden-5-yl)oxy]acetate.

Step B. Methyl {[6,7-dichloro-2-isopropyl-1-oxo-2-(3-oxobutyl)-2,3-dihydro-1H-inden-5-yl]oxy}acetate Methyl [(6,7-dichloro-2-isopropyl-1-oxo-2,3-dihydro-1H-inden-5-yl)oxy]acetate (16.5 gm., 0.05 mole) is suspended in dry tetrahydrofuran (100 ml.) containing triton-B (1 ml.). The suspension is stirred at ambient temperature and methyll vinyl ketone (5.02 gm., 0.072 mole) is added. The solution which becomes warm initially, is stirred at ambient temperature for 4 hours. Then, the stirring solution is treated with methyl vinyl ketone (0.3 ml.) and triton-B (0.6 ml.) every 4 hours for the next twenty hours.

The reaction mixture is evaporated in vacuo at 50° C. and the residual material dissolved in ether (100 ml.). The ether solution is washed with (two 20 ml. portions), dried over anhydrous magnesium sulfate and filtered. The filtrate is evaporated in vacuo and the residue triturated with ether (10 ml.), filtered and dried. The product is methyl [6,7-dichloro-2-isopropyl-1-oxo-2-(3-oxobutyl)-2,3-dihydro-1H-inden-5-yl]oxy acetate.

Step C. Methyl [(5,6-dichloro-9a-isopropyl-3-oxo-1,2,9,9a-tetrahydro-3H-floren-7-yl)oxy]acetate A mixture of methyl [(6,7-dichloro-2-isopropyl-1-oxo-2-(3-oxobutyl)-2,3-dihydro-1H-inden-5-yl)oxy]acetate (9.3 gm., 0.024 mole), potassium tert.-butoxide (2.70 gm., 0.024 mole) and tert.-butyl alcohol (100 ml.) is heated at 85° C. for three hours. The solution is concentrated in vacuo at 50° C. to obtain the crude product.

The product is subjected to column chromatography on silica gel (300 gm.) using a mixture of dichloromethane and tetrahydrofuran (100/4 v./v.) as the eluent. The product is pure methyl [(5,6-dichloro-9a-isopropyl-3-oxo-1,2,9,9a-tetrahydro-3H-fluoren-7-yl)-oxy]acetate.

Step D. [(5,6-Dichloro-9a-isopropyl-3-oxo-1,2,9,9a-tetrahydro-3H-fluoren-7-yl)oxy]acetic acid Methyl [(5,6-dichloro-9a-isopropyl-3-oxo-1,2,9,9a-tetrahydro-3H-fluoren-7yl)oxy]acetate (4.2 gm., 0.011 mole) is added to a solution composed of 20% aqueous sodium hydroxide solution (4.32 ml., 0.022 mole) and methanol (45 ml.). The mixture is stirred and heated at reflux for two hours and then concentrated in vacuo at 50° C. The residue is dissolved in water (50 ml.) and made acid to Congo red paper with 6 normal hydrochloric acid. The solid that separates is removed by filtration, washed with water, then with a little methanol and finally with a little ether. After drying, the product is recrystallized from acetic acid to give pure [(5,6-dichloro-9a-isopropyl-3-oxo-1,2,9,9a-tetrahydro-3H-fluoren-7-yl)oxy]acetic acid. Using a procedure similar to that described in Example 25, except that in Step A there is substituted for the [(6,7-dichloro-2-isopropyl-1-oxo-2,3-dihydro-1H-inden-5-yl)oxy]acetic acid, an equimolar amount of:

EXAMPLE 26

Step A. [(6,7-Dichloro-2-cyclopentyl-1-oxo-2,3-dihydro-1H-inden-5-yl)oxy]acetic acid.

EXAMPLE 27

Step A. [(6,7-Dichloro-1-oxo-2-phenyl-2,3-dihydro-1H-inden-5-yl)oxy]acetic acid.

EXAMPLE 28

Step A. [(2-Benzyl-6,7-dichloro-1-oxo-2,3-dihydro-1H-inden-5-yl)oxy]acetic acid.

In Examples 26, Step A through 28, Step A, the reaction is carried out as described in Example 25, Step A, there is obtained:

EXAMPLE 26

Step A. Methyl [(6,7-dichloro-2-cyclopentyl-1-oxo-2,3-dihydro-1H-inden-5-yl)oxy]acetate.

EXAMPLE 27

Step A. Methyl [(6,7-dichloro-1-oxo-2-phenyl-2,3-dihydro-1H-inden-5-yl)oxy]acetate.

EXAMPLE 28

Step A. Methyl [(2-benzyl-6,7-dichloro-1-oxo-2,3-dihydro-1H-inden-5-yl)oxy]acetate.

In Example 25, Step B, the starting material is the product from Step A. Using the products from step A of Example 26, 27 and 28 as starting materials but conducting the reaction as in Example 25, Step B, there is obtained:

EXAMPLE 26

Step B: Methyl {[[6,7-dichloro-2-cyclopentyl-1-oxo-2-(3-oxobutyl)-2,3-dihydro-1H-inden-5-yl]oxy]}acetate

EXAMPLE 27

Step B. Methyl {[6,7-dichloro-1-oxo-2-(3-oxobutyl)-2-phenyl-2,3-dihydro-1H-inden-5-yl]oxy}acetate.

EXAMPLE 28

Step B. Methyl {[2-benzyl-6,7-dichloro-1-oxo-2-(3-oxobutyl)-2,3-dihydro-1H-inden-5-yl]oxy}acetate.

Using the products from Step B of Example 26, 27, 28 as starting material in place for the Example 25, Step B, and conducting the reaction as in Example 25, Step C there is obtained:

EXAMPLE 26

Step C. Methyl [(5,6-dichloro-9a-cyclopentyl-3-oxo-1,2,9,9a-tetrahydro-3H-fluoren-7-yl)oxy]acetate.

EXAMPLE 27

Step C. Methyl [(5,6-dichloro-3-oxo-9a-phenyl-1,2,9,9a-tetrahydro-3H-fluoren-7-yl)oxy]acetate.

EXAMPLE 28

Step C: Methyl [(9a-benzyl-5,6-dichloro-3-oxo-1,2,9,9a-tetrahydro-3H-fluoren-7-yl)oxy]acetate.

EXAMPLE 28

Step C: Methyl [(9a-benzyl-5,6-dichloro-3-oxo-1,2,9,9a-tetrahydro-3H-fluoren-7-yl)oxy]acetate.

Using the products from Step C of Examples 26, 27 and 28 as starting materials in place of the product from Example 25, Step C and conducting the reaction as in Example 25, Step D, there is obtained:

EXAMPLE 26

Step D. [(5,6-Dichloro-9a-cyclopentyl-3-oxo-1,2,9,9a-tetrahydro-3H-fluoren-7-yl)oxy]acetic acid.

EXAMPLE 27

Step D. [(5,6-Dichloro-3-oxo-9a-phenyl-1,2,9, 9a-tetrahydro-3H-fluoren-7-yl)oxy]acetic acid.

EXAMPLE 28

Step D. [(9a-Benzyl-5,6-dichloro-3-oxo-1,2,9,9a-tetrahydro-3H-fluoren-7-yl)oxy]acetic acid.

EXAMPLE 29

[(5,6-Dichloro-3-oxo-2-vinyl-1,2,9,9a-tetrahydro-3H-fluoren-7-yl)-oxy]acetic acid.

Step A. Methyl [(6,7-dichloro-2-ethylidene-1-oxo-2,3-dihydro-1H-inden-5-yl)oxy]acetate

[(6,7-Dichloro-2-ethylidene-1-oxo-2,3-dihydro-1H-inden-5-yl)oxy]acetic acid (U.S. Pat. No. 3,704,314) (30.1 gm., 0.1 mole) is dissolved in methanol (150 ml.) and conc. sulfuric acid (0.5 ml.) added. The mixture is stirred and refluxed for 2 hours. The solvent is removed in vacuo by evaporation on a rotary evaporator and the residue dissolved in ethyl ether, washed with water and dried over sodium sulfate. The ether is removed by evaporation in vacuo in a rotary evaporator to give methyl [(6,7-dichloro-2-ethylidene-1-oxo-2,3-dihydro-1H-inden-5-yl)oxy]acetate.

Step B. Methyl [6,7-dichloro-1-oxo-2-(3-oxobutyl)-2-vinyl-2,3-dihydro-1H-inden-5-yl]oxy acetate.

Methyl (6,7-dichloro-2-ethylidene-1-oxo-2,3-dihydro-1H-inden-5-yl)oxy]acetate (25.4 gm., 0.08 mole) is dissolved in 1,2-dimethoxyethane (350 ml.) which had been boiled and cooled under dry nitrogen. Maintaining an atmosphere of dry nitrogen, the solution is cooled to 0° C. and potassium tert.-butoxide (900 mg., 0.008 mole) is added. Keeping the temperature at 0°, methyl vinyl ketone (11.2 gm., 0.16 mole) is added with stirring over 30 minutes. After stirring 2 hours at 0° C., the reaction mixture is allowed to warm to ambient temperature overnight. The solvent is removed in vacuo in a rotary evaporator, and the residue dissolved in ether, washed with water and dried over anhydrous magnesium sulfate. Evaporation of the ether in vacuo gave methyl [6,7-dichloro-1-oxo-2-3-oxobutyl)-2-vinyl-2,3-dihydro-1H-inden-5-yl]oxy acetate.

Step C. Methyl [(5,6-dichloro-3-oxo-9a-vinyl-1,2,9,9a-tetrahydro-3H-fluoren-7-yl)oxy]acetate A mixture of methyl {[[6,7-dichloro-1-oxo-(3-oxobutyl)-2-vinyl-2,3-dihydro-1H-inden-5-yl)oxy}-acetate (9.0 gm., 0.024 mole), pyrrolidine (1.70 gm., 0.024 mole) and acetic acid (1.42 gm., 0.024 mole) in toluene (100 ml.) is heated at 85° C. for one hour. The solution is concentrated in vacuo at 50° C. to obtain the crude product.

The product is subjected to column chromatography on silica gel (300 gm.) using a mixture of dichloromethane and tetrahydrofuran (100/4 v./v.) as the eluent. The product is methyl [(5,6-dichloro-3-oxo-9a-vinyl-1,2,9,9a-tetrahydro-3H-fluoren-7-yl)-oxy]acetate.

Step D. [(5,6-Dichloro-3-oxo-9a-vinyl-1,2,9,9a-tetrahydro-3H-fluoren-7-yl)oxy]acetic acid Methyl [(5,6-dichloro-3-oxo-9a-vinyl-1,2,9,9a-tetrahydro-3H-fluoren-7-yl)oxy]acetate (4.0 gm., 0.011 mole) is added to a solution composed of 20% aqueous sodium hydroxide solution (4.32 ml., 0.022 mole) and methanol (45 ml.). The mixture is stirred and heated at reflux for two hours and then concentrated in vacuo at 50° C. The residue is dissolved in water (50 ml.) and made acid to Congo red paper with 6 normal hydrochloric acid. The solid that separates is removed by filtration, washed with water, then with a little methanol and finally with a little ether. After recrystallization from acetic acid, there is obtained pure [(5,6-dichloro-3-oxo-9a-vinyl-1,2,9,9a-tetrahydro-3H-fluoren-7-yl)oxy]acetic acid.

Alternatively, [(5,6-dichloro-3-oxo-9a-vinyl-1,2,9,9a-tetrahydro-3H-fluoren-7-yl)oxy]acetic acid may be produced by the following process.

Methyl{[6,7-dichloro-1-oxo-2-(3-oxobutyl)-2-vinyl-2,3-dihydro-1H-inden-5-yl}acetate (7.3 gm., 0.02 mole) is dissolved in a solution of methanol (100 ml) and water (50 ml.) containing sodium hydroxide (9.43 gm., 0.236 mole), taking care to keep the temperature below 25° C. The solution is kept at ambient temperature for 48 hours. The solution is concentrated in vacuo to 100 ml. in a rotary evaporator at room temperature and poured into water (250 ml.) containing concentrated hydrochloric acid (26 ml.) with cooling. The product is separated by filtration, washed with water, dried and recrystallized from a mixture of acetic acid and water to obtain [(5,6-dichloro-3-oxo-9a-vinyl-1,2,9,9a-tetrahydro-3H-fluoren-7-yl)oxy]acetic acid.

EXAMPLE 30

[(5,6-Dichloro-9a-cyclopropyl-3-oxo-1,2,9,9a-tetrahydro-3H-fluoren-7-yl)oxy]acetic acid Step A. Ethyl [(5,6-dichloro-3-oxo-9a-vinyl-1,2,9,9a-tetrahydro-3H-fluoren-7-yl)oxy]acetate.

A solution of [(5,6-dichloro-3-oxo-9a-vinyl-1,2,9,9a-tetrahydro-3H-fluoren-7-yl-oxy]acetic acid (Example 29, Step D) (8.82 g., 0.025 mole) absolute ethanol (300 ml) and 12 N HCl (5 ml) in ethanol (20 ml) is heated under reflux on the steam bath with stirring for an hour. The excess solvent is removed under reduced pressure. Ice and water are added to the oily residue and the product extracted into methylene chloride. After drying over MgSO4, the solution is concentrated to yield the product.

Recrystallization from tetrahydrofuran-ether-petroleum ether (1:1:2) gives ethyl [(5,6-dichloro-3-oxo-9a-vinyl-1,2,9,9a-tetrahydro-3H-fluoren-7-yl)oxy]acetate.

Step B. Ethyl [(5,6-Dichloro-9a-cyclopropyl-3-oxo-1,2,9,9a-tetrahydro-3H-fluoren-7-yl)oxy]acetate To a hot, rapidly stirred solution of cupric acetate monohydrate (7.0 gm., 0.02 mole) in glacial acetic acid is added zinc dust (70 gm., 1.08 gm. atom). After about 30 seconds, all the copper has deposited on the zinc. The couple is allowed to settle for 0.5 to 1 minute, then as much as possible of the acetic acid is decanted, care being taken not to lose the silt-like couple. The dark reddish-gray couple is then washed with one 100 ml. portion of acetic acid followed by three 200 ml. portions of tetrahydrofuran.

A mixture of the zinc-copper couple, prepared as described above, (48 gm.) and methylene iodide (37.5 gm.) in tetrahydrofuran (300 ml.) is heated under reflux in a nitrogen atmosphere for an hour. Ethyl [(5,6-dichloro-3-oxo-9a-vinyl-1,2,9,9a-tetrahydro-3H-fluoren-7-yl)oxy]-acetate (8.2 gm., 0.02 mole) is added to the cooled mixture and stirring continued at 25° C. for 24 hours. The mixture is diluted with toluene (200 ml.), filtered and the filtrate is washed successively with saturated aqueous solutions of ammonium chloride and sodium bicarbonate and then with water. The organic lager is dried over anhydrous magnesium sulfate and the solvent removed using a rotary evaporator at reduced pressure. The residue is purified by column chromatography using a silica-gel column to give ethyl [(5,6-dichloro-9a-cyclopropyl-3-oxo-1,2,9,9a-tetrahydro-3H-fluoren-7-yl)oxy]-acetate.

Step C. [(5,6-Dichloro-9a-cyclopropyl-3-oxo-1,2,9,9a-tetrahydro-3H-fluoren-7-yl)oxy]acetic acid Ethyl [(5,6-dichloro-9a-cyclopropyl-3-oxo-1,2,9,9a-tetrahydro-3H-fluoren-7yl)oxy]acetate (4.2 gm., 0.011 mole) is added to a solution composed of 20% aqueous sodium hydroxide solution (4.32 ml., 0.022 mole) and methanol (45 ml.). The mixture is stirred and heated at reflux for two hours and then concentrated in vacuo at 50° C. The residue is dissolved in water (50 ml.) and made acid to Congo red paper with 6 normal hydrochloric acid. The solid that separates is removed by filtration, washed with water, then with a little methanol and finally with a little ether. After drying, the product is recrystallized from acetic acid to give pure

[(5,6-dichloro-3-oxo-9a-cyclopropyl-1,2,9,9a-tetrahydro-3H-fluoren-7-yl)oxy]acetic acid.

EXAMPLE 31

Resolution of
[(5,6-dichloro-9a-ethyl-3-oxo-1,2,9,9a-tetrahydro-3H-fluoren-7-yl)oxy]acetic acid Step A. A mixture of racemic [(5,6-dichloro-9a-ethyl-3-oxo-1,2,9,9a-tetrahydro-3H-fluoren-7-yl)oxy]-acetic acid (7.1 gm., 0.02 mole) and dextro(+)cinchonine (5.89 gm., 0.02 mole) is dissolved in the minimum volume of boiling acetonitrile, is cooled to 5° C. and aged for 48 hours. The crystalline product is removed by filtration and recrystallized twice from the minimum volume of acetonitrile. (The mother liquors from each recrystallization are combined and saved).

The pure salt is suspended in water (40 ml.) treated with 6 normal hydrochloric acid (5 ml.) and the precipitate that forms is removed by filtration and dried. This pure (+) enantiomer of [(5,6-dichloro-9a-ethyl-3-oxo-1,2,9,9a-tetrahydro-3H-fluoren-7-yl)-oxy]acetic is then recrystallized from a mixture of tetrahydrofuran and ethyl ether, m.p. 238°–240° C.;

$\alpha_{23}\cdot^{589}$ (C=1.1),+151.2.

Step B. The combined acetonitrile mother liquors from Step A are evaporated at reduced pressure and the residue treated with water (50 ml.) and 6 normal hydrochloric acid (7.5 ml.). The resulting precipitate is removed by filtration and dried.

This residual partially resolved [(5,6-dichloro-9a-methyl-3-oxo-1,2,9,9a-tetrahydro-3H-fluoren-7-yl)oxy]acetic acid (2.86 gm., 0.0118 mole) is treated with 1(−)cinchonidine (3.47 gm., 0.0118 mole) and the mixture dissolved in the minimum quantity of acetonitrile. After cooling for 48 hours, the salt that separates is removed by filtration and recrystallized twice from the minimum volume of acetonitrile. The pure salt is suspended in water (50 ml), treated with 6 normal hydrochloric acid (5 ml) and the precipitate that separates is removed by filtration and dried. This solid is recrystallized from a miture of tetrahydrofuran and ethyl ether to give the (−) enantiomer of [(5,6-dichloro-9a-ethyl-3-oxo-1,2,9,9a-tetrahydro-3H-fluoren-7-yl)oxy]acetic acid, m.p. 239°–241° C., $\alpha_{23}\cdot^{589}$ (C=1.1)=−151.2°.

EXAMPLE 32

Steps A and B. The Two Enantiomers of [(9a-butyl-5,6-dichloro-3-oxo-1,2,9,9a-tetrahydro-3H-fluoren-7-yl)oxy]acetic acid.

Carrying out the resolution as described in Example 31 except that the racemic [(5,6-dichloro-9a-ethyl-3-oxo-1,2,9,9a-tetrahydro-3H-fluoren-7-yl)oxy]-acetic acid (Example 1, Step E) is substituted by an equimolar quantity of racemic [(9a-butyl-5,6-dichloro-3-oxo-1,2,9,9a-tetrahydro-3H-fluoren-7-yl)oxy]acetic acid (Example 6, Step E), there is obtained the two enantiomers of [(9a-butyl-5,6-dichloro-3-oxo-1,2,9,9a-tetrahydro-3H-fluoren-7-yl)oxy]acetic acid.

EXAMPLE 33

Steps A and B. The Two Enantiomers of [(9a-allyl-5,6-dichloro-3-oxo-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy]-acetic acid is replaced by an equimolar quantity of racemic [(9a-allyl-5,6-dichloro-3-oxo-1,2,9,9a-tetrahydro-3H-fluoren-7-yl)oxy]acetic acid (Example 47, Step L) there is obtained the two enantiomers of [(9a-allyl-5,6-dichloro-3oxo-1,2,9,9a-tetrahydro-3H-fluoren-7-yl)-oxo]acetic acid.

EXAMPLE 34

Steps A and B. The Two Enantiomers of [(5,6-dichloro-3-oxo-9a-propargyl-1,2,9,9a-tetrahydro-3H-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy-acetic acid is replaced by an equimolar quantity of racemic [(5,6-dichloro-3-oxo-9a-propargyl-1,2,9,9a-tetrahydro-3H-fluoren-7-yl)oxy]acetic acid (Example 48, Step L), there is obtained the two enantiomers of [(5,6-dichloro-3-oxo-9a-propargyl-1,2,9,9a-tetrahydro-3H-fluoren-7-yl)oxy]acetic acid.

EXAMPLE 35

Steps A and B. The two enantiomers of [(5,6-dichloro-9a-cyclopropylmethyl-3-oxo-1,2,9,9a-tetrahydro-3H-fluoren-7-yl)oxy]acetic acid.

Carrying out the resolution as described in Example 31, except that the racemic [(5,6-dichloro-9a-ethyl-3-oxo-1,2,9,9a-tetrahydro-3H-fluoren-7-yl)oxy]acetic acid (Example 1, Step E) is substituted by an equimolar quantity of racemic [(5,6-dichloro-9a-cyclopropylmethyl-3-oxo-1,2,9,9a-tetrahydro-3H-fluoren-7-yl)oxy]acetic acid (Example 50, Step L), there is obtained the two enantiomers of [(5,6-dichloro-9a-cyclopropylmethyl-3-oxo-1,2,9,9a-tetrahydro-3H-fluoren-7-yl)oxy]acetic acid.

EXAMPLE 36

Steps A and B. The two enantiomers of [(9a-benzyl-5,6-dichloro-3-oxo-1,2,9,9a-tetrahydro-3H-fluoren-7-yl)oxy]acetic acid.

Carrying out a reaction as described in Example 31, except that the racemic [(5,6-dichloro-9a-ethyl-3-oxo-1,2,9,9a-tetrahydro-3H-fluoren-7-yl)oxy]acetic acid (Example 1, Step E) is substituted by an equimolar quantity of racemic [(9a-benzyl-5,6-dichloro-3-oxo-1,2,9,9a-tetrahydro-3H-fluoren-7-yl)oxy]acetic acid (Example 9, Step E), there is obtained the two enantiometers of [(9a-benzyl-5,6-dichloro-3-oxo-1,2,9,9a-tetrahydro-3H-fluoren-7-yl)-oxy]acetic acid.

EXAMPLE 37

Steps A and B. The two enantiomers of [(5,6-dichloro-3-oxo-9a-propyl-1,2,9,9a-tetrahydro-3H-fluoren-7-yl)oxy]acetic acid.

Carrying out the resolution as described in Example 31, except that the racemic [(5,6-dichloro-9a-ethyl-3-oxo-1,2,9,9a-tetrahydro-3H-fluoren-7-yl)oxy]acetic acid is substituted by an equimolar quantity of [(5,6-dichloro-3-oxo-9a-propyl-1,2,9,9a-tetrahydro-3H-fluoren-7-yl)oxy]acetic acid (Example 4, Step E) there is obtained the two enantiomers of [(5,6-dichloro-3-oxo-9a-propyl-1,2,9,9a-tetrahydro-3H-fluoren-7-yl)oxy]acetic acid.

EXAMPLE 38

Steps A and B. The two enantiomers of [(5,6-dichloro-3-oxo-1,2,9,9a-tetrahydro-3H-fluoren-7-yl)oxy]-acetic acid Carrying out the resolution as described in Example 31, except that the racemic [(5,6-dichloro-9a-ethyl-3-oxo-1,2,9,9a-tetrahydro-3H-fluoren-7-yl)oxy]-acetic acid is replaced by an equimolar quantity of racemic [(5,6-dichloro-3-oxo-1,2,9,9a-tetrahydro-3H-fluoren-7-yl)-oxy]acetic acid (Example 2, Step E), there is obtained the two enantiomers of [(5,6-dichloro-3-oxo-1,2,9,9a-tetrahydro-3H-fluoren-7-yl)oxy]acetic acid.

Example 39

Steps A and B. The two enantiomers of [(5,6-dichloro-9a-methyl-3-oxo-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy-acetic acid is replaced by an equimolar quantity of racemic [(5,6-dichloro-9a-methyl-3-oxo-1,2,9,9a-tetrahydro-3H-fluoren-7-yl)oxy]acetic acid (Example 3, Step E), there is obtained the two enantiomers of [(5,6-dichloro-9a-methyl-3-oxo-1,2,9,9a-tetrahydro-3H-fluoren-7-yl)oxy]acetic acid.

EXAMPLE 40

Steps A and B. The two Enantiomers of [(5,6-dichloro-9a-isopropyl-3-oxo-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy]acetic acid is replaced by an equimolar quantity of racemic [(5,6-dichloro-9a-isopropyl-3-oxo-1,2,9,9a-tetrahydro-3H-floren-7-yl)oxy]acetic acid (Example 25, Step D), there is obtained the two enantiomers of [(5,6-dichloro-9a-isopropyl-3-oxo-1,2,9,9a-tetrahydro-3H-fluoren-7-yl)oxy]acetic acid.

EXAMPLE 41

Steps A and B. The two enantiomers of [(5,6-dichloro-9a-cyclopentyl-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy]acetic acid is replaced by an equimolar quantity of racemic [(5,6-dichloro-9a-cyclopentyl-3-oxo-1,2,9,9a-tetrahydro-3H-fluoren-7-yl)oxy]acetic acid (Example 26, Step D), there is obtained the two enantiomers of [(5,6-dichloro-9a-cyclopentyl-3-oxo-1,2,9,9a-tetrahydro-3H-fluoren-7-yl)oxy]acetic acid.

EXAMPLE 42

Steps A and B. The two enantiomers of [(5,6-dichloro-3-oxo-9a-vinyl-1,2,9,9a-tetrahydro-3H-fluoren-7-yl)oxy]acetic acid Carrying out the resolution as described in Example 31, except that the racmic [(5,6-dichloro-9a-ethyl-3-oxo-1,2,9,9a-tetrahydro-3H-fluoren-7-yl)oxy]acetic acid is replaced by an equimolar quantity of racemic [(5,6-dichloro-3-oxo-9a-vinyl-1,2,9,9a-tetrahydro-3H-fluoren-7-yl)oxy]acetic acid (Example 29, Step D), there is obtained the two enantiomers of [(5,6-dichloro-3-oxo-9a-vinyl-1,2,9,9a-tetrahydro-3H-fluoren-7-yl)oxy]acetic acid.

EXAMPLE 43

Steps A and B. The two enantiomers of [(5,6-dichloro-9a-cyclopropyl-3-oxo-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy]-acetic acid is replaced by an equimolar quantity of racemic [(5,6-dichloro-9a-cyclopropyl-3-oxo-1,2,9,9a-tetrahydro-3H-fluoren-7-yl)oxy]acetic acid (Example 30, Step D), there is obtained the two enantiomers of [(5,6-dichloro-9a-cyclopropyl-3-oxo-1,2,9,9a-tetrahydro-3H-fluoren-7-yl)oxy]acetic acid.

EXAMPLE 44

Steps A and B. The two enantiomers of [(5,6-dichloro-3-oxo-9a-phenyl-1,2,9,9a-tetrahydro-3H-fluoren-7-yl)oxy]acetic acid Carrying out the resolution as described in Example 31, except that the racemic [(5,6-dichloro-9a-ethyl-3-oxo-1,2,9,9a-tetrahydro-3H-fluoren-7-yl)oxy]-acetic acid is replaced by an equimolar quantity of racemic [(5,6-dichloro-3-oxo-9a-phenyl-1,2,9,9a-tetrahydro-3H-fluoren-7-yl)oxy]acetic acid (Example 27, Step D), there is obtained the two enantiomers of [(5,6-dichloro-3-oxo-9a-phenyl-1,2,9,9a-tetrahydro-3H-fluoren-7-yl)oxy]acetic acid.

EXAMPLE 45

1-[(5,6-Dichloro-9a-methyl-3-oxo-1,2,9,9a-tetrahydro-3H-fluoren-7-yl)oxy]cyclopentane-1-carboxylic acid Step A. 5,6-Dichloro-7-hydroxy-9a-methyl-1,2,9,9a-tetrahydro-3H-fluoren-3-one.

Carrying out a reaction as described in example 1, Step C, except that the 5,6-dichloro-9a-ethyl-7-methoxy-1,2,9,9a-tetrahydro-3H-fluoren-3-one is replaced by an equimolar quantity of [(5,6-dichloro-oxy]acetic acid (Example 3, Step E), there is obtained 5,6-dichloro-7-hydroxy-9a-methyl-1,2,9,9a-tetrahydro-3H-fluoren-3-one.

Step B. Ethyl 1-[(5,6-Dichloro-9a-methyl-3-oxo-1,2,9,9a-tetrahydro-3H-fluoren-7-yl)oxy]cyclopentane-1-carboxylate.

Carrying out a reaction as described in Example 1, Step D, except that the 5,6-dichloro-9a-ethyl-7-hydroxy-1,2,9,9a-tetrahydro-3H-fluoren-3-one and ethyl bromoacetate are replaced by equimolar quantities of 5,6-dichloro-7-hydroxy-9a-methyl-1,2,9,9a-tetrahydro-3H-fluoren-3-one and ethyl 1-bromocyclopentane-1-carboxylate, there is obtained ethyl 1-[(5,6-dichloro-9a-methyl-3-oxo-1,2,9,9a-tetrahydro-3H-fluoren-7-yl)oxy]cyclopentane-1-carboxylate.

Step C. 1-[(5,6-Dichloro-9a-methyl-3-oxo-1,2,9,9a-tetrahydro-3H-fluoren-7-yl)oxy]cyclopentane-1-carboxylic acid.

Carrying out a reaction as described in Example 1, Step E, except that the ethyl [(5,6-dichloro-9a-ethyl-1,2,9,9a-tetrahydro-3H-fluoren-7-yl)oxy]acetate is replaced by an equimolar quantity of ethyl 1-[(5,6-dichloro-9a-methyl-3-oxo-1,2,9,9a-tetrahydro-3H-fluoren-7-yl)oxy]cyclopentane-1-carboxylate, to give 1-[(5,6-dichloro-9a-methyl-3-oxo-1,2,9,9a-tetrahydro-3H-fluoren-7-yl)oxy]cyclopentane-1-carboxylic acid.

EXAMPLE 46

Fluoro[(5,6-dichloro-9a-ethyl-3-oxo-1,2,9,9a-tetrahydro-3H-fluoren-7-yl)oxy]acetic acid Step A. 5,6-Dichloro-9a-ethyl-7-hydroxy-1,2,9,9a-tetrahydro-3H-fluoren-3-one.

Carrying out a reaction as described in Example 1, Step C, except that the 5,6-dichloro-9a-ethyl-7-methoxy-1,2,9,9a-tetrahydro-3H-fluoren-3-one is replaced by an equimolar quantity of [(5,6-dichloro-9a-ethyl-3-oxo-1,2,9,9a-tetrahydro-3H-fluoren-7-yl)oxy]acetic acid (Example 20, Step D), there is obtained 5,6-dichloro-9a-ethyl-7-hydroxy-1,2,9,9a-tetrahydro-3H-fluoren-3-one.

Step B. Ethyl fluoro[(5,6-dichloro-9a-ethyl-3-oxo-1,2,9,9a-tetrahydro-3H-fluoren-7-yl)oxy]acetate.

Carrying out a reaction as described in Example 1, Step D, except that the ethyl bromoacetate is replaced by an equimolar quantity of ethyl bromofluoroacetate, there is obtained ethyl fluoro[(5,6-dichloro-9a-ethyl-3-oxo-1,2,9,9a-tetrahydro-3H-fluoren-7-yl)oxy]acetate.

Step C. Fluoro[(5,6-dichloro-9a-ethyl-3-oxo-1,2,9,9a-tetrahydro-3H-fluoren-7-yl)oxy]acetic acid.

Ethyl fluoro[(5,6-dichloro-9a-ethyl-3-oxo-1,2,9,9a-tetrahydro-3H-fluoren-7-yl)oxy]acetate (4.01 gm., 0.02 mole) is dissolved in ethanol (75 ml.) and treated with a solution of sodium bicarbonate (3.36 gm., 0.04 mole) in water (150 ml.). The mixture is heated and stirred on a steam bath for 15 minutes and then concentrated in vacuo to a volume of 50 ml. The residual solution is diluted with water (50 ml.) and acidified to Congo red test paper with 6 normal hydrochloric acid. The precipitate that forms is removed by filtration, washed with water and dried. The product is sufficiently pure for use but it may be further purified by recrystallization from a mixture of acetic acid and water to produce pure fluoro[(5,6-dichloro-9a-ethyl-3-oxo-1,2,9,9a-tetrahydro-3H-fluoren-7-yl)oxy]acetic acid.

EXAMPLE 47

[(9a-Allyl-5,6-dichloro-3-oxo-1,2,9,9a-tetrahydro-3H-fluoren-7-yl)oxy]acetic acid Step A. 2,3-Dichloro-4-methoxybenzaldehyde.

A mixture of 2,3-dichloro-4-hydroxybenzaldehyde (19.1 gm., 0.1 mole) and potassium carbonate (34.4 gm., 0.25 mole) in dimethylformamide (50 ml.) is stirred and treated dropwise over 15 minutes with dimethyl sulfate (14.1 gm., 0.11 mole). The reaction is exothermic; after 45 minutes the mixture is poured with stirring into water (300 ml.). The solid product that separates is removed by filtration, washed with water and then washed with a little methanol. After drying the yield of 2,3-dichloro-4-methoxybenzaldehyde is 16 gm., m.p. 117°–118° C.

Step B. 2,3-Dichloro-4-methoxycinnamic acid

A mixture of 2,3-dichloro-4-methoxybenzaldehyde (158 gm., 0.77 mole), malonic acid (146 gm., 1.4 mole), pyridine (450 ml.) and piperidine (15 ml.) is heated and stirred on a steam bath for 2¾ hours. the hot reaction mixture is poured, with stirring into a mixture of concentrated hydrochloric acid (770 ml.) and crushed ice (3.1 kg.).

The solid that separates is removed by filtration, then washed, first with water and then with a little methanol. After drying, the solid is dissolved in a solution containing sodium hydroxide (61.6 gm.) and water (7.7 liters). The insoluble material is removed by filtration and the filtrate acidified with concentrated hydrochloric acid.

The solid 2,3-dichloro-4-methoxycinnamic acid that separates is removed by filtration, washed with water and dried. The yield is 179 gm. (96%, m.p. 246°–249° C. This crude material is adequate for use in the next step.

Step C. 3-(2,3-Dichloro-4-methoxyphenyl)propanoic acid.

2.3 Dichloro-4-methoxycinnamic acid (200.8 g., 0.813 mole) is dissolved in tetrahydrofuran (1600 ml.) and 5% platinum on charcoal (16.3 gm.) is added. The mixture is divided into 8 separate units and each is placed in a Parr hydrogenation apparatus in an atmosphere of hydrogen at an initial pressure of 50 p.s.i. Upon shaking, the time required for the reduction of each batch is 35 to 60 minutes.

The combined reaction mixtures are filtered and the solvent removed by distillation at reduced pressure to give crude 3-(2,3-dichloro-4-methoxyphenyl)propanoic acid, 176.3 gm., m.p. 141°–143° C. The material is adequate for use in the next step.

Step D. 4,5-Dichloro-6-methoxy-2,3-dihydro-1H-inden-1-one.

3-(2,3-Dichloro-4-methoxyphenyl)propanoic acid (176.3 gm., 0.708 mole) is placed in benzene (500 ml.) and thionyl chloride (101.8 ml., 1.42 mole) is added. The mixture is refluxed for 1½ hours and the volatile materials removed by distillation at reduced pressure. The residual oil is dissolved in benzene (50 ml.) and the solvent again removed at reduced pressure. This process is repeated and the residue is dissolved in dry methylene chloride (500 ml.).

The solution is placed in a flask protected from atmospheric moisture by a calcium chloride drying tube and cooled via an ice bath. Then aluminum chloride (94.4 gm., 0.708 mole) is added portionwise via a vessel attached to the reaction flask by Gooch rubber tubing. After the addition is complete, the cooling bath is removed and stirring at ambient temperature is continued for 3 hours.

The reaction mixture is poured, with stirring into ice water (1635 ml.) containing concentrated hydrochloric acid (218 ml.). The solid that separates is collected by filtration, washed with water and dried. The yield is 160 gm. This material is recrystallized (while treating with decolorizing charcoal) from acetonitrile to give 4,5-dichloro-6-methoxy-2,3-dihydro-1H-inden-1-one, 129.1 gm., m.p. 163°–165°.

Step E. 4,5-Dichloro-6-methoxy-2,3-dihydro-1H-indene.

An amalgam of zinc, prepared from zinc (65 gm.) and mercuric chloride (3.5 gm.), is stirred with a mixture of water (20 ml.), ethanol (20 ml.) and concentrated hydrochloric acid (50 ml.). The mixture is heated to boiling and a slurry of 4,5-dichloro-6-methoxy-2,3-dihydro-1H-inden-1-one (23.1 gm., 0.1 mole) in a mixture of hot ethanol (150 ml.), water (20 ml.) and concentrated hydrochloric acid (50 ml.) is added over 15 minutes. Then the boiling mixture is treated with concentratred hydrochloric acid (50 ml.) over an hour. Boiling and stirring is continued for 5 hours longer and then the stirring is terminated and the mixture is cooled. The liquid portion is separated by decantation and concentrated to half its volume in vacuo. The solid portion of the reaction mixture is extracted with ether (four 50 ml. portions). The combined ether extracts and liquid portion of the reaction mixture are united in a separatory funnel and water (250 ml.) is added. The mixture is thoroughly shaken and the ether layer separated, washed with water, then with brine and finally dried over anhydrous magnesium sulfate. Evaporation of the ether gives 15.2 g. of crude 4.5-dichloro-6-methoxy-2,3-dihydro-1H-indene, m.p. 78°-82° C. This material is adequate for use in the next step.

Step F. 6,7-Dichloro-5-methoxy-2,3-dihydro-1H-inden-1-one.

4,5-Dichloro-6-methoxy-2,3-dihydro-1H-indene (21 gm., 0.097 mole) is dissolved in acetic acid (280 ml.) and chromium trioxide (14 gm., 0.14 mole) in a mixture of water (15 ml.) and acetic acid (40 ml.) is added dropwise with stirring over a period of one hour. The mixture is poured, with stirring into cold water (1200 ml.) and the solid that separates is removed by filtration, washed with water and dried. The product, which consists of a mixture of the desired material and the isomer described in Step D, is subjected to column chromatographic separation using 225 gm. of silica gel and chloroform is used for elution. Evaporation of the solvent gives 6,7-dichloro-5-methoxy-2,3-dihydro-1H-inden-1-one, 5.2 gm., m.p. 154°-156° C.

Step G. 2-Allyl-6,7-dichloro-5-methoxy-2,3-dihydro-1H-inden-1-one.

6,7-Dichloro-5-methoxy-2,3-dihydro-1H-inden-1-one (63.5 gm., 0.274 mole) is dissolved in a mixture of dry tert.-butyl alcohol (500 ml.) and dry benzene (1.5 liters). The solution is refluxed and potassium tert.-butoxide (46 gm., 0.301 mole) in dry tert.-butyl alcohol (1 liter) is added as rapidly as possible. The solution is refluxed for another ½ hour, cooled to 20° C., stirred and treated with allky bromide (36 gm., 0.301 mole). The mixture is stirred and refluxed for 4 hours, cooled and treated with water (250 ml.). The crude 2-allyl-6,7-dichloro-5-methoxy-2,3-dihydro-1H-inden-1-one is separated by filtration, washed with water, dried and recrystallized from a mixture of benzene and hexane.

Step H. 2-Allyl-6,7-dichloro-5-hydroxy-2,3-dihydro-1H-inden-1-one.

Dry pyridine hydrochloride (500 gm.) is melted and heated to 195° C. and 2-allyl-6,7-dichloro-5-methoxy-2,3-dihydro-1H-inden-1-one (45.4 gm., 0.167 mole) is added with stirring. The reaction mixture is kept at 95° C. for 45 minutes and then poured with vigorous stirring into crushed ice (2 kg.). The crude product is collected by filtration, washed with water and dried. The 2-allyl-6,7-dichloro-5-hydroxy-2,3-dihydro-1H-inden-1-one is recrystallized from a mixture of ethanol and water.

Step I. Ethyl [(2-allyl-6,7-dichloro-1-oxo-2,3-dihydro-1H-inden-5-yl)oxy]acetate.

Carrying out a reaction as described in Example 1, Step D, except that the 5,6-dichloro-9a-ethyl-7-hydroxy-1,2,9,9a-tetrahydro-3H-fluoren-3-one is replaced by an equimolar quantity of 2-allyl-6,7-dichloro-5-hydroxy-2,3-dihydro-1H-inden-1-one, there is obtained ethyl [(2-allyl-6,7-dichloro-1-oxo-2,3-dihydro-1H-inden-5-yl)oxy]acetate.

Step J. Ethyl {[2-allyl-6,7-dichloro-1-oxo-2-(3-oxybutyl)-2,3-dihydro-1H-inden-5-yl]oxy}acetate.

Carrying out a reaction as described in example 20, Step B, except that the methyl [(6,7-dichloro-2-ethyl-1-oxo-2,3-dihydro-1H-inden-5-yl)oxy]acetate is replaced by an equimolar quantity of ethyl [(2-allyl-6,7-dichloro-1-oxo-2,3-dihydro-1H-inden-5-yl)oxy]acetate, there is obtained ethyl [2-allyl-6,7-dichloro-1-oxo-2-(3-oxobutyl)-2,3-dihydro-1H-inden-5-yl]oxy acetate.

Step K. Ethyl [(9a-allyl-5,6-dichloro-3-oxo-1,2,9,9a-tetrahydro-3H-fluoren-7-yl)oxy]acetate.

Carrying out a reaction as described in Example 20, Step C, except that the methyl [6,7-dichloro-2-ethyl-1-oxo-2-(3-oxobutyl)-2,3-dihydro-1H-inden-5-yl]oxy acetate is replaced by an equimolar quantity of ethyl (2-allyl-6,7-dichloro-1-oxo-2-(3-oxobutyl)-2,3-dihydro-1H-inden-5-yl)oxy)acetate, there is obtained ethyl [(9a-allyl-5,6-dichloro-3-oxo-1,2,9,9a-tetrahydro-3H-fluoren-7-yl)oxy]acetate.

Step L. [(9a-Allyl-5,6-dichloro-3-oxo-1,2,9,9a-tetrahydro-3H-fluoren-7-yl)oxy]acetic acid.

Carrying out a reaction as described in Example 20, Step D, except that the methyl [(5,6-dichloro-9a-ethyl-3-oxo-1,2,9,9a-tetrahydro-3H-fluoren-7-yl)oxy]acetate is replaced by an equimolar quantity of ethyl [(9a-allyl-5,6-dichloro-3-oxo-1,2,9,9a-tetrahydro-3H-fluoren-7-yl)oxy]acetate, there is obtained [(9a-allyl-5,6-dichloro-3-oxo-1,2,9,9a-tetrahydro-3H-fluoren-7-yl)oxy]acetic acid.

EXAMPLE 48

[(5,6-Dichloro-3-oxo-9a-propargyl-1,2,9,9a-tetra-3H-fluoren-7-yl)oxy]acetic acid By carrying out a series of reactions as described in Example 47, except that in Step G, the allyl bromide is replaced by an equimolar quantity of propargyl bromide and using the product from each step in the subsequent step, there is obtained:

Step G. 6,7-Dichloro-5-methoxy-2-propargyl-2,3-dihydro-1H-inden-1-one.

Step H. 6,7-Dichloro-5-hydroxy-2-propargyl-2,3-dihydro-1H-inden-1-one.

Step I. Ethyl [(6,7-dichloro-1-oxo-2-propargyl-2,3-dihydro-1H-inden-5-yl)oxy]acetate.

Step J. Ethyl [6,7-dichloro-1-oxo-2-(3-oxobutyl)-2-propargyl-2,3-dihydro-1H-inden-5-yl]oxy acetate.

Step K. [5,6-Dichloro-3-oxo-9a-propargyl-1,2,9,9a-tetrahydro-3H-fluoren-7-yl)oxy]acetate.

Step L. [(5,6-Dichloro-3-oxo-9a-propargyl-1,2,9,9a-tetrahydro-3H-fluoren-7-yl)oxy]acetic acid.

EXAMPLE 49

[(5,6-Dichloro-9a-(2-methylpropyl)-3-oxo-1,2,9,9a-tetrahydro-3H-fluoren-7-yl)oxy]acetic acid Carrying out a series of reactions as described in Example 47, except that in Step G, the allyl bromide is replaced by an equimolar quantity of 2-methylpropyl bromide, and using the product from each step in the subsequent one, there is obtained:

Step G. 6,7-Dichloro-2-(2-methylpropyl)-5-methoxy-2,3-dihydro-1H-inden-1-one.

Step H. 6,7-Dichloro-2-(2-methylpropyl)-5-hydroxy-2,3-dihydro-1H-inden-1-one.

Step I. Ethyl {[6,7-dichloro-2-(2-methylpropyl)-1-oxo-2,3-dihydro-1H-inden-5-yl)oxy]}acetate.

Step J. Ethyl [6,7-dichloro-2-(2-methylpropyl)-1-oxo-2-(3-oxobutyl)-2,3-dihydro-1H-inden-5-yl]oxy acetate.

Step K. Ethyl [5,6-dichloro-9a-(2-methylpropyl)-3-oxo-1,2,9,9a-tetrahydro-3H-fluoren-7-yl]oxy acetate.

Step L. [5,6-Dichloro-9a-(2-methylpropyl)-3-oxo-1,2,9,9a-tetrahydro-3H-fluoren-7-yl]oxy acetic acid.

EXAMPLE 50

[(5,6-Dichloro-9a-cyclopropylmethyl-3-oxo-1,2,9,9a-tetrahydro-3H-fluoren-7-yl)oxy]acetic acid Carrying out a series of reactions as described in Example 47, except that in Step G, the allyl bromide is replaced by an equimolar quantity of (bromomethyl)cyclopropane, and using the product from each step in the subsequent step, there is obtained:

Step G. 6,7-Dichloro-2-cyclopropylmethyl-5-methoxy-2,3-dihydro-1H-inden-1-one.

Step H. 6,7-Dichloro-2-cyclopropylmethyl-5-hydroxy-2,3-dihydro-1H-inden-1-one.

Step I. Ethyl [(6,7-dichloro-2-cyclopropylmethyl-1-oxo-2,3-dihydro-1H-inden-5-yl)oxy]acetate.

Step J. Ethyl {[6,7-dichloro-2-cyclopropylmethyl-1-oxo-2-(3-oxobutyl)-2,3-dihydro-1H-inden-5-yl]oxy}acetate.

Step K. Ethyl [(5,6-dichloro-9a-cyclopropylmethyl-3-oxo-1,2,9,9a-tetrahydro-3H-fluoren-7-yl)oxy]acetate.

Step L. [(5,6-Dichloro-9a-cyclopropylmethyl-3-oxo-1,2,9,9a-tetrahydro-3H-fluoren-7-yl)oxy]acetic acid.

EXAMPLE 51

[(5,6-Dichloro-9a-ethyl-3-oxo-1,2,9,9a-tetrahydro-3H-fluoren-7-yl)oxy]acetic acid 5,6-Dichloro-9a-ethyl-7-hydroxy-1,2,9,9a-tetrahydro-3H-fluoren-3-one, (Example 1, Step C) (15 gm., 0.048 mole), potassium carbonate (13.3 gm., 0.096 mole), dimethylformamide (100 ml.) and iodoacetic acid (10.6 gm., 0.057 mole) is stirred at room temperature for 24 hours. The reaction mixture is poured into water (150 ml.), stirred, warmed to 50° C., filtered and the filtrate acidified with 6 N hydrochloric acid to obtain [(5,6-dichloro-9a-ethyl-3-oxo-1,2,9,9a-tetrahydro-3H-fluoren-7-yl)oxy]acetic acid, which after recrystallization from acetic acid, melts at 237° C.–238° C.

EXAMPLE 52

[(5,6-Dichloro-9a-methyl-3-oxo-1,2,9,9a-tetrahydro-3H-fluoren-7-yl)oxy]acetic acid Carrying out a reaction as described in Example 51, except that the 5,6-dichloro-9a-ethyl-7-hydroxy-1,2,9,9a-tetrahydro-3H-fluoren-3-one is replaced by an equivalent quantity of 5,6-dichloro-7-hydroxy-9a-methyl-1,2,9,9a-tetrahydro-3H-fluoren-3-one (Example 3, Step C), and there is obtained [(5,6-dichloro-9a-methyl-3-oxo-1,2,9,9a-tetrahydro-3H-fluoren-7-yl)oxy]acetic acid.

EXAMPLE 53

[(5,6-Dichloro-9a-ethyl-3-oxo-1,2,9,9a-tetrahydro-3H-fluoren-7-yl)oxy]acetic acid Step A. tert.-Butyl [(5,6-dichloro-9a-ethyl-3-oxo-1,2,9,9a-tetrahydro-3H-fluoren-7-yl)oxy]acetate.

A mixture of 5,6-dichloro-9a-ethyl-7-hydroxy-1,2,9,9a-tetrahydro-3H-fluoren-3-one (Example 1, Step C) (15 gm., 0.048 mole), tert.-butyl bromoacetate (10.3 gm., 0.0528 mole), potassium carbonate (13.3 gm., 0.096 mole) and dimethylformamide (100 ml.) is stirred at 35° C. for an hour and then cooled and poured into water (100 ml.). The solid that separates is tert.-butyl [(5,6-dichloro-9a-ethyl-3-oxo-1,2,9,9a-tetrahydro-3H-fluoren-7-yl)oxy]acetate, which is separated by filtration, washed with water and dried. This material is adequate for use in the next step.

Step B. [(5,6-Dichloro-9a-ethyl-3-oxo-1,2,9,9a-tetrahydro-3H-fluoren-7-yl)oxy]acetic acid.

Tert.-butyl [(5,6-dichloro-9a-ethyl-3-oxo-1,2,9,9a-tetrahydro-3H-fluoren-7-yl)oxy]acetate (8.22 gm., 0.02 mole) in benzene (100 ml.) containing p-toluenesulfonic acid (0.6 gm.) is refluxed for 20 minutes. The solid that separates upon cooling is [(5,6-dichloro-9a-ethyl-3-oxo-1,2,9,9a-tetrahydro-3H-fluoren-7-yl)oxy]acetic acid, m.p. 237° C.–238° C.

EXAMPLE 54

[(5,6-Dichloro-3-oxo-9a-propyl-1,2,9,9a-tetrahydro-3H-fluoren-7-yl)oxy]acetic acid Step A. Tert.-butyl [(5,6-dichloro-3-oxo-9a-propyl-1,2,9,9a-tetrahydro-3H-fluoren-7-yl)oxy]acetate.

Carrying out a reaction as described in Example 53, Step A, except that the 5,6-dichloro-9a-ethyl-7-hydroxy-1,2,9,9a-tetrahydro-3H-fluoren-3-one is replaced by an equimolar quantity of 5,6-dichloro-7-hydroxy-9a-propyl-1,2,9,9a-tetrahydro-3H-fluoren-3-one (Example 4, Step C), thereby is obtained tert.-butyl 8-(5,6-dichloro-3-oxo-9a-propyl-1,2,9,9a-tetrahydro-3H-fluoren-7-yl)oxy]acetate.

Step B. [(5,6-Dichloro-3-oxo-9a-propyl-1,2,9,9a-tetrahydro-3H-fluoren-7-yl)oxy]acetic acid.

Carrying out a reaction as described in Example 53, Step B, except that the tert.-butyl [(5,6-dichloro-9a-ethyl-3-oxo-1,2,9,9a-tetrahydro-3H-fluoren-7-yl)oxy]acetate is replaced by an equimolar amount of tert.-butyl [(5,6-dichloro-3-oxo-9a-propyl-1,2,9,9a-tetrahydro-3H-fluoren-7-yl)oxy]acetate, thereby is obtained [(5,6-dichloro-3-oxo-9a-propyl-1,2,9,9a-tetrahydro-3H-fluoren-7-yl)oxy]acetic acid.

EXAMPLE 55

Benzyl [(5,6-Dichloro-9a-ethyl-3-oxo-1,2,9,9a-tetrahydro-3H-fluoren-7-yl)oxy]acetate Methyl [(5,6-dichloro-9a-ethyl-3-oxo-1,2,9,9a-tetrahydro-3H-fluoren-7-yl)oxy]acetate (Example 20, Step C) (5.8 g., 0.016 mole) is dissolved in a mixture of dry benzyl alsohol (50 ml) and methylene chloride (40 ml.) containing amberlite IRA 400 (ethoxide) (5–6 g.). The mixture is stirred magnetically at reflux for four hours and then filtered. The filtrate is concentrated in vacuo to give a yellow solid (5.3 g.) which upon trituration with ethanol and washing with ether yields the product.

EXAMPLE 56

Ethyl [(5,6-dichloro-9a-ethyl-3-oxo-1,2,9,9a-tetrahydro-3H-fluoren-7-yl)oxy]acetate A solution of [(5,6-dichloro-9a-ethyl-3-oxo-1,2,9,9a-tetrahydro-3H-fluoren-7-yl)oxy]acetic acid (Example 20, Step D) (0.15 g., 0.004 mole) absolute ethanol (60 ml) and 12 N HCl (5 ml.) in ethanol (20 ml.) is heated under reflux on the steam bath with stirring for an hour. The excess solvent is removed under reduced pressure. Ice and water are added to the oily residue and the product extracted into ether. After drying over MgSO4, the solution is concentrated to yield 1.6 g. of product, m.p. 160°–162° C.

Recrystallization from tetrahydrofuran-ether-petroleum ether (1:1:2) gives 1.15 g. of ethyl [(5,6-dichloro-9a-ethyl-3-oxo-1,2,9,9a-tetrahydro-3H-fluoren-7yl)oxy]acetate, m.p. 164°–166° C.

By carrying out the reaction as described in Example 56, except that the ethanol is replaced by an equal amount of:

EXAMPLE 57

1-Propanol

EXAMPLE 58

Isopropyl alcohol

EXAMPLE 59

1-Butanol

EXAMPLE 60

Cyclobutanol

EXAMPLE 61

Allyl alcohol

EXAMPLE 62

Propargyl alcohol
There is obtained:

EXAMPLE 57

Propyl [(5,6-dichloro-9a-ethyl-3-oxo-1,2,9,9a-tetrahydro-3H-fluoren-7-yl)oxy]acetate.

EXAMPLE 58

Isopropyl [(5,6-dichloro-9a-ethyl-3-oxo-1,2,9,9a-tetrahydro-3H-fluoren-7-yl)oxy]acetate.

EXAMPLE 59

Butyl [(5,6-dichloro-9a-ethyl-3-oxo-1,2,9,9a-tetrahydro-3H-fluoren-7-yl)oxy]acetate.

EXAMPLE 60

Cyclobutyl [(5,6-dichloro-9a-ethyl-3-oxo-1,2,9,9a-tetrahydro-3H-fluoren-7-yl)oxy]acetate.

EXAMPLE 61

Allyl [(5,6-dichloro-9a-ethyl-3-oxo-1,2,9,9a-tetrahydro-3H-fluoren-7-yl)oxy]acetate.

EXAMPLE 62

Propargyl [(5,6-dichloro-9a-ethyl-3-oxo-1,2,9,9a-tetrahydro-3H-fluoren-7-yl)oxy]acetate.

By carrying out the reaction as described in Example 56 except that the [(5,6-dichloro-9a-ethyl-3-oxo-1,2,9,9a-tetrahydro-3H-fluoren-7-yl)oxy]acetic acid is replaced by an equimolar amount of:

EXAMPLE 63

(+) [(5,6-Dichloro-9a-ethyl-3-oxo-1,2,9,9a-tetrahydro-3H-fluoren-7-yl)oxy]acetic acid (Example 31, Step A).

EXAMPLE 64

(−) [(5,6-Dichloro-9a-ethyl-3-oxo-1,2,9,9a-tetrahydro-3H-fluoren-7-yl)oxy]acetic acid (Example 31, Step B).
There is obtained:

EXAMPLE 63

Ethyl (+) [(5,6-dichloro-9a-ethyl-3-oxo-1,2,9,9a-tetrahydro-3H-fluoren-7-yl)oxy]acetate, m.p. 94°–97° C.

EXAMPLE 64

Ethyl (−) [(5,6-dichloro-9a-ethyl-3-oxo-1,2,9,9a-tetrahydro-3H-fluoren-7-yl)oxy]acetate, m.p. 94°–97° C.

EXAMPLE 65

Carboxymethyl [(5,6-dichloro-9a-ethyl-3-oxo-1,2,9,9a-tetrahydro-3H-fluoren-7-yl)oxy]acetate Step A. Benzyloxycarbonylmethyl [(5,6-dichloro-9a-ethyl-3-oxo-1,2,9,9a-tetrahydro-3H-fluoren-7-yl)oxy]acetate A mixture containing [(5,6-dichloro-9a-ethyl-3-oxo-1,2,9,9a-tetrahydro-3H-fluoren-7-yl)oxy]acetic acid (Example 20, Step D) (1.07 g, 0.003 mole), potassium carbonate (0.41 g, 0.003 mole) and benzyl bromoacetate (0.69 g, 0.003 mole) in dimethylformamide (35 ml) is heated at 80° C. for two hours. Then this mixture is filtered and the filtrate is concentrated in vacuo. The residue is dissolved in methylene chloride, washed with aqueous sodium bicarbonate and then water, dried over anhydrous magnesium sulfate and concentrated in vacuo to give a viscous oil which is triturated with ether to give 1.06 g. of product.

Step B. Carboxymethyl [(5,6-dichloro-9a-ethyl-3-oxo-1,2,9,9a-tetrahydro-3H-fluoren-7-yl)oxy]acetate Benzyloxycarbonylmethyl [(5,6-dichloro-9a-ethyl-3-oxo-1,2,9,9a-tetrahydro-3H-fluoren-7-yl)oxy]acetate (1.0 g, 0.002 mole) (Step A) is dissolved in tetrahydrofuran (35 ml) and hydrogenated at ambient temperatures and atmospheric pressure employing 10% Pd/C (0.05 g.) as the catalyst in 2 hours. The catalyst is filtered through super-cel in an atmosphere of nitrogen. Then the filtrate is concentrated in vacuo at 50° C. to give the product (0.74 g) which is purified by recrystallization from methanol (9 ml) to yield 0.50 g of product, m.p. 179°–181° C.

By carrying out the reaction as described in Example 65, Step A, except that the benzyl bromoacetate is replaced by an equimolar quantity of:

EXAMPLE 66

Step A. Benzyl 5-bromopentanoate

EXAMPLE 67

Step A. Benzyl 2-bromopropanoate

EXAMPLE 68

Step A. Benzyl 4-bromobutanoate
There is obtained:

EXAMPLE 66

Step A. 4-(Benzyloxycarbonyl)butyl [(5,6-dichloro-9a-ethyl-3-oxo-1,2,9,9a-tetrahydro-3H-fluoren-7-yl)oxy]acetate.

EXAMPLE 67

Step A. 1-(Benzyloxycarbonyl)ethyl [(5,6-dichloro-9a-ethyl-3-oxo-1,2,9,9a-tetrahydro-3H-fluoren-yl)oxy]acetate.

EXAMPLE 68

Step A. 3-(Benzyloxycarbonyl)propyl [(5,6-dichloro-9a-ethyl-3-oxo-1,2,9,9a-tetrahydro-3H-fluoren-7-yl)oxy]acetate.

By carrying out the reaction as described in Example 65, Step B, except that the benzyloxycarbonylmethyl [(5,6-dichloro-9a-ethyl-3-oxo-1,2,9,9a-tetrahydro-3H-fluoren-7-yl)oxy]acetate is replaced separately by the compounds produced in Example 66, Step A, Example 67, Step A, and in Example 68, Step A, there is produced:

EXAMPLE 66

Step B. 4-Carboxybutyl [(5,6-dichloro-9a-ethyl-3-oxo-1,2,9,9a-tetrahydro-3H-fluoren-7-yl)oxy]acetate.

EXAMPLE 67

Step B. 1-Carboxyethyl [(5,6-dichloro-9a-ethyl-3-oxo-1,2,9,9a-tetrahydro-3H-fluoren-7-yl)oxy]acetate.

EXAMPLE 68

Step B. 3-Carboxypropyl [(5,6-dichloro-9a-ethyl-3-oxo-1,2,9,9a-tetrahydro-3H-fluoren-7-yl)oxy]acetate.

By carrying out the reaction as described in Example 65, Step A, except that the [(5,6-dichloro9-a-ethyl-3-oxo-1,2,9,9a-tetrahydro-3H-fluoren-7-yl)oxyl]acetic acid is replaced by an equimolar quantity of:

EXAMPLE 69

Step A. (+) [(5,6-Dichloro-9a-ethyl-3-oxo1,2,9,9a-tetrahydro-3H-fluoren-7oxy]acetic acid (Example 31), there is obtained:

EXAMPLE 69

Step A. Benzyloxycarbonylmethyl (+) [(5,6-dichloro-9a-ethyl-3-oxo-1,2,9,9a-tetrahydro-3H-fluoren7-yl)oxy]acetate.

By carrying out the reaction as described in Example 65, Step B, except that the benzyloxycarbonylmethyl [(5,6-dichloro-9a-ethyl-3-oxo-1,2,9,9a-tetrahydro3H-fluoren-7-yl)oxyl]acetate is replaced by the product of Example 69, Step A, there is obtained:

EXAMPLE 69

Step B. Carboxymethyl (+) [(5,6-dichloro9a-ethyl-3-oxo-1,2,9,9a-tetrahydro-3H-fluoren-7-yl)oxy]-acetate.

EXAMPLE 70

1-Carboxy-1-methylethyl (+) [(5,6-dichloro-9a-ethyl-3-oxo-1,2,9,9a-tetrahydro-3H-fluoren-7-yl(oxy]acetate Step A. (+) 1-{[(5,6-dichloro-9a-ethyl-3-oxo-1,2,9,9a-tetrahydro-3H-fluoren-7-yl)oxy]acetyl}-imidazole.

(+) [(5,6-Dichloro-9a-ethyl-3-oxo-1,2,9,9a-tetrahydro-3H-fluoren-7-yl)oxy]acetic acid (Example 31, Step A) (0.71 g., 0.002 mole) is suspended in dry tetrahydrofuran (20 ml) and cooled to 0° C. A solution of 1,1'-carbonyldiimidazole (0.32 g, 0.002 mole) in tetrahydrofuran (5 ml) is added. The solution of 1-{[(5,6-dichloro-9a-ethyl-3-oxo-1,2,9,9-a-tetrahydro-3H-fluoren-7-yl)oxy]acetyl}imidazole that is formed is used in the next step without isolation.

Step B. 1-Carboxy-1-methylethyl (+) [(5,6-dichloro-9a-ethyl-3-oxo-1,2,9,9a-tetrahydro-3H-fluoren7-yl)oxy-]acetate To the solution of (+) {[(5,6-dichloro-9a-ethyl-3-oxo-1,2,9,9a-tetrahydro-3H-fluoren-7-oxy]acetyl}-imidazole (0.002 mole) prepared in Step A at 0° C. is added with stirring 2-hydroxyisobutyric acid (0.21 g., 0.002 mole). After stirring overnight at the ambient temperature, the colorless reaction mixture is concentrated in vacuo at 50° C. The resultant yellow liquid is chromatographed using a silica-gel (60 gm) column and eluted with a mixture of methylene chloride and isopropyl alcohol (100/5 v.v.). The product is obtained by evaporation of the solvent in vacuo.

By carrying out the reaction as described in Example 70, Steps A and B, except that the (+) [(5,6-dichloro-9a-ethyl-3-oxo-1,2,9,9a-tetrahydro-3H-fluoren7-yl)oxy]acetic acid is replaced by an equimolar amount of:

EXAMPLE 71

(+) [(5,6-Dichloro-3-oxo-1,2,9,9-a-tetrahydro-3H-fluoren-7-yl)oxy]acetic acid (Example 38, Step A).

EXAMPLE 72

(+) [(5,6-Dichloro-9a-methyl-3-oxo-1,2,9,9-a-tetrahydro3H-fluoren-7-yl)oxyl]acetic acid (Example 39, Step A).

EXAMPLE 73

(+) [(5,6-Dichloro-3-oxo-9a-propyl-1,2,9,9a-tetrahydro-3H-fluoren-7-yl)oxy]acetic acid (Example 37, Step A).

EXAMPLE 74

(+) [(5,6-Dichloro-9a-isopropyl-3-oxo-1,2,9,9a-tetrahydro-3H-fluoren-7-yl)oxy]acetic acid (Example 40, Step A).

EXAMPLE 75

(+) [(9a-Butyl-5,6-dichloro-3-oxo-1,2,9,9-a-tetrahydro-3H-fluoren-7-yl)oxy]acetic acid (Example 32, Step A).

EXAMPLE 76

(+) [(5,6-Dichloro-9a-cyclopropyl-3-oxo-1,2,9,9a-tetrahydro-3H-fluoren-7-yl)oxy]acetic acid (Example 43, Step A).

EXAMPLE 77

(+) [(5,6-Dichloro-9a-cyclopropylmethyl-3-oxo-1,2,9,9-a-tetrahydro-3H-fluoren-7-yl)oxy]acetic acid (Example 35, Step A).

EXAMPLE 78

(+) [(5,6-Dichloro-9a-cyclopentyl-3-oxo1,2,9,9a-tetrahydro-3H-fluoren-7-yl)oxy]acetic acid (Example 41, Step A).

EXAMPLE 79

(+) [(5,6-Dichloro-3-oxo-9a-vinyl-1,2,9,9a-tetrahydro-3H-fluoren-7-yl)oxy]acetic acid (Example 42, Step A).

EXAMPLE 80

(+) [(9a-Allyl-5,6-dichloro-3-oxo-1,2,9,9-a-tetrahydro-3H-fluoren-7-yl)oxy]acetic acid (Example 33, Step A).

EXAMPLE 81

(+) [(5,6-Dichloro-3-oxo-9a-propargyl-1,2,9,9-a-tetrahydro-3H-fluoren-7-yl)oxy]acetic acid (Example 34, Step A).

EXAMPLE 82

(+) [(9a-Benzyl-5,6-dichloro-3-oxo-1,2,9,9a-tetrahydro-3H-fluoren-7-yl)oxy]acetic acid (Example 36, Step A).

EXAMPLE 71

1-Carboxy-1-methylethyl (+) [(5,6-dichloro3-oxo-1,2,9,9a-tetrahydro-3H-fluoren-7-yl)oxy ]acetate.

EXAMPLE 72

1-Carboxy-1-methylethyl (+) [(5,6-dichloro9a-methyl-3-oxo-1,2,9,9a-tetrahydro-3H-fluoren-7-yl)oxy]-acetate.

EXAMPLE 73

1-Carboxy-1-methylethyl (+) [(dichloro-3-oxo-9a-propyl-1,2,9,9a-tetrahydro-3H-fluoren-7-yl)oxy]acetate.

EXAMPLE 74

1-Carboxy-1-methylethyl (+) [(dichloro-9a-isopropyl-3-oxo-1,2,9,9-a-tetrahydro-3H-fluoren-7-yl)oxy]-acetate.

EXAMPLE 75

(1-Carboxy-1-methylethyl (+) [(9a-butyl-5,6-dichloro-3-oxo-1,2,9,9a-tetrahydro-3H-fluoren-7-yl)oxy]-acetate.

EXAMPLE 76

1-Carboxy-1-methylethyl (+) [(5,6-dichloro9a-cyclopropyl-3-oxo-1,2,9,9-a-tetrahydro-b  3H-fluoren-7-yl)oxy]acetate.

EXAMPLE 77

1-Carboxy-1-methylethyl (+) [(5,6-dichloro9a-cyclopropylmethyl-3-oxo-1,2,9,9-a-tetrahydro-3H-fluoren-7-yl)oxy]acetate.

EXAMPLE 78

1-Carboxy-1-methylethyl (+) [(5,6-dichloro-9a-cyclopentyl-3-oxo-1,2,9,9a-tetrahydro-3H-fluoren-7-yl)oxy]acetate.

EXAMPLE 79

1-Carboxy-1-methylethyl (+) [(5,6-dichloro3-oxo-9a-vinyl-1,2,9,9a-tetrahydro-3H-fluoren-7yl)oxy]acetate.

EXAMPLE 80

1-Carboxy-1-methylethyl (+) [(9a-allyl-5,6-dichloro-3-oxo-1,2,9,9a-tetrahydro-3H-fluoren-7-yl)oxy]acetate.

EXAMPLE 81

1-Carboxy-1-methylethyl (+) [(5,6-dichloro-3-oxo-9a-propargyl-1,2,9,9a-tetrahydro-3H-fluoren-7-yl)oxy]acetate.

EXAMPLE 82

1-Carboxy-1-methyethyl (+) [(9a-benzyl-5,6-dichloro-3-oxo-1,2,9,9a-tetrahydro-3H-fluoren-7-yl)oxy]acetate.

EXAMPLE 83

1-Carboxy-1-methylethyl (+) [(5,6-dichloro-3-oxo-9a-phenyl-1,2,9,9a-tetrahydro-3H-fluoren-7-yl)oxy]acetate.

EXAMPLE 84

2-(Morpholinyl)ethyl [(5,6-dichloro-9a-ethyl-3-oxo-1,2,9,9a-tetrahydro-3H-fluoren-7-yl)oxy]acetate Step A. 1-{[(5,6-dichloro-9a-ethyl-3-oxo-1,2,9,9a-tetrahydro-3H-fluoren-7-yl)oxy]acetyl}imidazole.

[(5,6-Dichloro-9a-ethyl-3-oxo-1,2,9,9a-tetrahydro-3H-fluoren-7-yl)oxy]acetic acid (Example 20, Step D) (0.71 g., 0.002 mole) is suspended in dry tetrahydrofuran (20 ml) and cooled to 0° C. A solution of 1,1'-carbonyldiimidazole (0.32 g, 0.002 mole) in tetrahydrofuran (5 ml) is added. The solution of 1-{[(5,6-dichloro-9a-ethyl-3-oxo-1,2,9,9a-tetrahydro-3H-fluoren-7-yl) oxy]acetyl}-imidazole that is formed is used in the next step without isolation.

Step B. 2-(4-Morpholinyl)ethyl [(5,6-dichloro-9a-ethyl-3-oxo-1,2,9,9a-tetrahydro-3H-fluoren-7-yl)oxy]acetate To the solution of 1-{[(5,6-dichloro-9a-ethyl-3-oxo-1,2,9,9a-tetrahydro-3H-fluoren-7-yl)oxy]acetyl}-imidazole (0.002 mole) prepared in Step A at 0° C. is added with stirring 4-(2-hydroxyethyl)morpholine (0.26 g., 0.002 mole) and a catalytic amount of sodium hydride (10 mg). After stirring overnight at the ambient temperature, the colorless reaction mixture is concentrated in vacuo at 50° C. The resultant yellow liquid is chromatographed using a silica-gel (60 gm) column and eluted with a mixture of methylene chloride and isopropyl alcohol (100/5 v.v.). The product is triturated with ether to give analyticaly pure product, 0.58 g, m.p. 133°–133.5° C.

By carrying out the reaction as described in Example 84 Step B, except that the 4-(2-hydroxyethyl)morpholine is replaced by an equimolar amount of:

EXAMPLE 85:

2-Dimethylaminethanol

EXAMPLE 86:

3-Diethylaminopropanol

EXAMPLE 87:

1-(2-Hydroxyethyl)pyrrolidine

EXAMPLE 88:

1-Methyl-3-hydroxypiperidine

EXAMPLE 89:

1-Methyl-4-hydroxypiperidine
there is obtained:

EXAMPLE 85

2-Dimethylaminoethyl [(5,6-dichloro-9a-ethyl3-oxo-1,2,9,9a-tetrahydro-3H-fluoren-7-yl)oxy]acetate.

EXAMPLE 86

3-Diethylaminopropyl [(5,6-dichloro-9a-ethyl-3-oxo-1,2,9,9a-tetrahydro-3H-fluoren-7-yl)oxy]acetate.

EXAMPLE 87

2-(1-pyrrolidinyl)ethyl [(5,6-dichloro-9a-ethyl-3-oxo-1,2,9,9a-tetrahydro-3H-fluoren-7-yl)oxy]acetate.

EXAMPLE 88

1-Methyl-3-piperidyl [(5,6-dichloro-9a-ethyl3-oxo-1,2,9,9a-tetrahydro-3H-fluoren-7-yl)oxy]acetate.

EXAMPLE 89

1-Methyl-4-piperidyl [(5,6-dichloro-9a-ethyl-3-oxo-1,2,9,9a-tetrahydro-3H-fluoren-7-yl)oxy]acetate.

EXAMPLE 90

(5-Hydroxymethyl-2-furyl)methyl [(5,6-dichloro-9a-ethyl-3-oxo-1,2,9,9a-tetrahydro-3H-fluoren-7-yl)oxy]acetate

[(5,6-dichloro-9a-ethyl-3-oxo-1,2,9,9a-tetrahydro-3H-fluoren-7-yl)oxy]acetic acid (Example 20, Step D) (1.43 g, 0.004 mole) is suspended in dry tetrahydrofuran (10 ml) and then triethylamine (0.401 g., 0.004 mole) is added. The resulting solution is cooled at 0° C. followed by the addition of ethyl chloroformate (0.438 g, 0.004 mole) in tetrahydrofuran (5 ml) to form the mixed anhydride and triethylamine hydrochloride which precipitates. To this mixture is added 2,5-di-(hydroxymethyl)-furan (1.03 g, 0.008 mole) in tetrahydrofuran (5 ml). The reaction mixture is then allowed to rise to ambient temperature before refluxing for one hour. The triethylamine hydrochloride that separates (0.55 g) is filtered and the filtrate is concentrated in vacuo to give a brown solid (2.71 g) which is purified by column chromatography over silica gel (100 g) by elution with a mixture of methylene chloride-tetrahydrofuran (100/4 v.v.) followed by a mixture of methylene-chloride-isopropanol (100/5 v.v.) to give 0.55 g. of product which is recrystallized first from isopropanol and then from acetonitrile to give an impure material which melts at 135.5°–137° C. This material is further purified by high pressure liquid chromatography using a Whatman Partsil M9 10/25 PAC column and methylene chloride-isopropyl alcohol (100/2 v.v.) at a flow rate of 5 ml./min. The yield of analytically pure product is 280 mg., m.p. 142°–143° C.

By carrying out the reaction as described in Example 90, except that the 2,5-di(hydroxymethyl)furan is replaced by an equimolar amount of:

EXAMPLE 91:

Dihydroxyacetone

EXAMPLE 92:

2-Ethoxyethanol

EXAMPLE 93:

Tetrahydrofurfuryl alcohol

EXAMPLE 94:

1,1,1-Tris(hydroxymethyl)ethane
there is obtained:

EXAMPLE 91

3-Hydroxy-2-oxopropyl [(5,6-dichloro-9-a-ethyl-3-oxo-1,2,9,9a-tetrahydro-3H-fluoren-7-yl)oxy]acetate.

EXAMPLE 92

2-Methoxyethyl [(5,6-dichloro-9a-ethyl-3-oxo-1,2,9,9a-tetrahydro-3H-fluoren-7-yl)oxy]acetate.

EXAMPLE 93

Tetrahydrofurfuryl [(5,6-dichloro-9a-ethyl-3-oxo-1,2,9,9a-tetrahydro-3H-fluoren-7-yl)oxy]acetate.

EXAMPLE 94

2,2-Bis(hydroxymethyl)propyl [(5,6-dichloro-9a-ethyl-3-oxo-1,2,9,9a-tetrahydro-3H-fluoren-7yl)oxy]acetate.

EXAMPLE 95

2-Oxopropyl [(5,6-Dichloro-9a-ethyl-3-oxo-1,2,9,9a-tetrahydro-3H-fluoren-7-yl)oxy]acetate Potassium carbonate (0.2 g) is suspended in a solution of [(5,6-dichloro-9a-ethyl-3-oxo-1,2,9,9a-tetrahydro-3H-fluoren-7-yl)oxy]acetic acid (Example 20, Step D) (0.4 g, 0.0011 mole) in dimethylformamide (3 ml). After warming the suspension on a steam bath for 15 minutes, chloroacetone (0.5 g, 0.005 mole) is added and the mixture heated for an additional 15 minutes. The reaction mixture is cooled, poured into water (50 ml) and the product extracted into ether (three 15 ml portions. The extract is dried over $Na_2SO_4$. After filtration, the extract is concentrated to give a yellow oil. Trituration with cold ether causes crystallization to occur. The crystalline product weighs 0.1 g and melts at 153°–155° C.

EXAMPLE 96

3-Hydroxypropyl [(5,6-Dichloro-9a-ethyl-3-oxo-1,2,9,9a-tetrahydro-3H-fluoren-7-yl)oxy]acetate By substitution of an equimolar amount of 3-bromo-1-propanol for the chloroacetone in Example 95, there is obtained a crude product which is column chromatographed on silica gel and eluted with a mixture of acetic acid, acetone and toleune (5/5/90 v.v.v.). The product weighs 100 mg and melts at 114°–117° C.

By carrying out the reaction as described in Example 95, except that the chloroacetone is replaced by an equimolar amount of:

EXAMPLE 97:

2Bromoethanol

EXAMPLE 98:

2-Bromo-1,3-propanediol

EXAMPLE 99:

2-Bromoethanesulfonamide

EXAMPLE 100:

1-Bromo-2,3-propanediol
there is obtained:

EXAMPLE 97

2-Hydroxyethyl [(5,6-dichloro-9a-ethyl-3-oxo-1,2,9,9a-tetrahydro-3H-fluoren-7-yl)oxy]acetate.

EXAMPLE 98

1-(Hydroxymethyl)-2-hydroxyethyl [(5,6-dichloro-9a-ethyl-3oxo-1,2,9,9a-tetrahydro-3H-fluoren-7-yl)oxy]acetate.

EXAMPLE 99

2-Sulfamoylethyl [(5,6-dichloro-9-a-ethyl-3-oxo-1,2,9,9a-tetrahydro-3H-fluoren-7-yl)oxy]acetate.

EXAMPLE 100

2,3-Dihydroxypropyl [(5,6-dichloro-9a-ethyl-3-oxo-1,2,9,9a-tetrahydro-3H-fluoren-7-yl)oxy]acetate.

EXAMPLE 101

3-Pyridylmethyl [(5,6-Dichloro-9a-ethyl-3-oxo-1,2,9,9a-tetrahydro-3H-fluoren-7-yl)oxy]acetate A mixture of methyl [(5,6-dichloro-9a-ethyl-3-oxo-1,2,9,9a-tetrahydro-3H-fluoren-7-yl)oxy]acetate (Example 20, Step C) (0.74 g, 0.002 mole), 3A molecular sieves (10 g) and 3-hydroxymethylpyridine (0.65 g, 0.006 mole) in methylene chloride (40 ml) is stirred at ambient temperature overnight.

The reaction mixture is then filtered through supercel and washed with methylene chloride. The filtrate is concentrated in vacuo at 50° C. This residue is chromatographed over silica gel (30 g) by elution with a methylene chloride-isopropanol mixture (100/3 v.v.) to give 0.36 g of product which is recrystallized from isopropanol (7 ml) to yield 0.23 g of product containing isopropanol. This sample is dried at 83° C. for 13 hours in vacuo to remove the solvent. The yield of product is 0.20 g., m.p. 120°–121° C.

By carrying out the reaction as described in Example 101 except that the 3-hydroxymethylpyridine is replaced by an equimolar quantity of:

EXAMPLE 102:

2-Hydroxymethylpyridine

EXAMPLE 103:

4-Hydroxymethylpyridine

EXAMPLE 104:

3-Hydroxymethylpyridine-N-oxide
there is obtained:

EXAMPLE 102

2-Pyridylmethyl [(5,6-dichloro-9a-ethyl-3-oxo-1,2,9,9a-tetrahydro-3H-fluoren-7-yl)oxy]acetate.

EXAMPLE 103

4-Pyridylmethyl [(5,6-dichloro-9a-ethyl-3-oxo-1,2,9,9a-tetrahydro-3H-fluoren-7-yl)oxy]acetate.

EXAMPLE 104

3-Pyridylmethyl [(5,6-dichloro-9a-ethyl-3-oxo-1,2,9,9a-tetrahydro-3H-fluoren-7-yl)oxy]acetate-N-oxide.

EXAMPLE 105

[(5,6-Dichloro-9a-ethyl-3-oxo-1,2,9,9a-tetrahydro-3H-fluoren-7-yl)oxy]acetic Acid Anhydride A stirred suspension of 5,6-dichloro-9a-ethyl-3-oxo-1,2,9,9a-tetrahydro-3H-fluoren-7-yl)oxy]acetic acid (14.2 gm., 0.04 mole) in methylene chloride (1.5 liters) is treated with a solution of N,N-dicyclohexylcarbodiimide (4.33 gm., 0.021 mole) in methylene chloride (100 ml.). After an hour, the solvent is removed by distillation and the residue treated with dry ether (150 ml.). The dicyclohexylurea is removed by filtration and the ether removed by evaporation at reduced pressure to give [(5,6-dichloro-9a-ethyl-3-oxo-1,2,9,9a-tetrahydro-3H-fluoren-7-yl)oxy]acetic acid anhydride.

EXAMPLE 106

[(5,6-Dichloro-9a-ethyl-3-oxo-1,2,9,9a-tetrahydro-3H-fluoren-7-yl)oxy]acetamide

1-{[(5,6-Dichloro-9a-ethyl-3-oxo-1,2,9,9a-tetrahydro-3H-fluoren-7-yl)oxy]acetyl}imidazole (Example 84, Step A) (0.81 gm, 0.002 mole) in tetrahydrofuran (20 ml) is treated with 25% aqueous ammonium hydroxide (5 ml). After warming for an hour at 35° C., the solvent is removed in vacuo whereby the product remains which is washed with water and recrystallized from acetic acid.

By carrying out the reaction as described in Example 106, except that the 25% aqueous ammonium hydroxide is replaced by:

EXAMPLE 107A:

(t-Butoxycarbonyl)methhylamine

EXAMPLE 108A:

2-(t-Butyoxycarbonyl)ethylamine
there is obtained:

EXAMPLE 107

Step A. N-(t-Butoxycarbonylmethyl)-[(5,6-dichloro-9a-ethyl-3-oxo-1,2,9,9a-tetrahydro-3H-fluoren-7-yl)oxy]acetamide

EXAMPLE 108

Step A. N-[2-(t-Butoxycarbonyl)ethyl]-[(5,6-dichloro-9a-ethyl-3-oxo-1,2,9,9a-tetrahydro-3H-fluoren-7-yl)oxy]acetamide.

EXAMPLE 107

Step B. N-Carboxymethyl [(5,6-dichloro-9a-ethyl-3-oxo-1,2,9,9a-tetrahydro-3H-fluoren-7-yl)oxy]acetamide. N-(t-Butyoxcarbonylmethyl)-[(5,6-dichloro-9a-ethyl-3-oxo-1,2,9,9a-tetrahydro-3H-fluoren-7-yl)oxy]acetamide (Example 107, Step A) (600 mg) is dissolved in toluene (100 ml), treated with p-toluenesulfonic acid (50 mg) and the mixture refluxed for 2 hours. The solvent is removed and the product dissolved in an aqueous sodium bicarbonate solution, filtered and acidified to Congo-red paper with dilute hydrochloric acid. The solid that seeparates is removed by filtration, washed with water and dried. The yield is 300 mg.

EXAMPLE 108

Step B. N-(2-Carboxyethyl)-[(5,6-dichloro-9a-ethyl-3-oxo-1,2,9,9a-tetrahydro-3H-fluoren-7-yl)oxy]acetamide By carrying out the reaction as described in Example 107, Step B, except that the N-(t-butoxycarbonylmethyl)-[(5,6-dichloro-9a-ethyl-3-oxo-1,2,9,9a-tetrahydro-3H-fluoren-7-yl)oxy]acetamide is replaced by an equimolar amount of N-[2-(t-butoxycarbonyl)ethyl]-[(5,6-dichloro-9a-ethyl-3-oxo-1,2,9,9a-tetrahydro-3H-fluoren-7-yl)oxy]acetamide. There is obtained N-(2-carboxyethyl)-[(5,6-dichloro-9a-ethyl-3-oxo-1,2,9,9a-tetrahydro-3H-fluoren-7-yl)oxy]acetamide.

EXAMPLE 109

2,3-Dihydroxypropyl [(5,6-Dichloro-9a-ethyl-3-oxo-1,2,9,9a-tetrahydro-3H-fluoren-7-yl)oxy]acetate Step A. (2,2-Dimethyl-1,3-dioxolan-4-yl)methyl [(5,6-dichloro-9a-ethyl-3-oxo-1,2,9,9a-tetrahydro-3H-fluoren-7-yl)oxy]acetate A mixture of 2 gm. of [(5,6-dichloro-9a-ethyl-3-oxo-1,2,9,9a-tetrahydro-3H-fluoren-7-yl)oxy]acetic acid, 3 ml. of 2,2-dimethyl-4-hydroxymethyl-1,3-dioxolane and 0.5 g. of p-toluenesulfonic acid hydrate are heated on the steam bath for 3 hours. The darkreaction mixture then is chromatographed on 300 g of silica, and eluted with acetic acid-acetone-toluene (5:5:90). Fractions containing a single component (Rf~0.4) are pooled and concentrated to a yellow oil. On standing overnight, a mixture of crystalline solid and yellow oil resulted. The mixture is filtered and the solid recrystallized from tetrahydrofuran-ether-petroleum ether (5:15:25). The yield of pure product is 0.3 g., m.p. 143°–145° C.

Step B. 2,3-Dihydroxypropyl [(5,6-dichloro-9a-ethyl-3-oxo-1,2,9,9a-tetrahydro-3H-fluoren-7-yl)oxy]acetate A mixture of 165 mg of (2,2-dimethyl-1,3-dioxolan-4-yl)methyl [(5,6-dichloro-9a-ethyl-3-oxo-1,2,9,9a-tetrahydro-3H-fluoren-7-yl)oxy]acetate from Example 109, Step A is dissolved in 100 ml. of 0.075 N hydrochloric acid and 20 ml. of acetone and heated, with stirring at 50°–55° C. for 2 hours. The mixture is cooled and neutralized with a solution of sodium bicarbonate. The solution is saturated with sodium chloride and extracted two times with 100 ml. portions of 20% tetrahydrofuran in ether. The extract is dried over $Na_2SO_4$. After filtration, the filtrate was concentrated to a yellow oil that solidified on standing. After recrystallization from tetrahydrofuran-ether-petroleum ether, there is obtained 110 mg. of product, m.p. 135°–138° C.

EXAMPLE 110

1-(Hydroxymethy)-2-hydroxyethyl [(5,6-Dichloro-9a-ethyl-3-oxo-1,2,9,9a-tetrahydro-3H-fluoren-7-yl)oxy]acetate Step A. (2-Phenyl-1,3-dioxan-5-yl) [(5,6-dichloro-9a-ethyl-3-oxo-1,2,9,9a-tetrahydro-3H-fluoren-7-yl)oxy]acetate By substituting the 2,2-dimethyl-4-hydroxymethyl-1,3-dioxolane used in Example 109, Step A, with an equimolar quantity of 5-hydroxy-2-phenyl-1,3-dioxane and conducting the reaction as described in Example 109, Step A, there is obtained (2-phenyl-1,3-dioxan-5-yl) [(5,6-dichloro-9a-ethyl-3-oxo-1,2,9,9a-tetrahydro-3H-fluoren-7-yl)oxy]acetate.

Step B. 1-(Hydroxymethyl)-2-hydroxyethyl [(5,6-dichloro-9a-ethyl-3-oxo-1,2,9,9a-tetrahydro-3H-fluoren-7-yl)oxy]acetate By substituting the (2,2-dimethyl-1,3-dioxolan-4-yl)methyl [(5,6-dichloro-9a-ethyl-3-oxo-1,2,9,9a-tetrahydro-3H-fluoren-7-yl)oxy]acetate used in Example 109, Step B by an equimolar amount of (1-phenyl-1,3-dioxan-5-yl) [(5,6-dichloro-9a-ethyl-3-oxo-1,2,9,9a-tetrahydro-3H-fluoren-7-yl)oxy]acetate and conducting the reaction as described in Example 109, Step B, there is obtained 1-(hydroxymethyl)-2-hydroxyethyl [(5,6-dichloro-9a-ethyl-3-oxo-1,2,9,9a-tetrahydro-3H-fluoren-7-yl)oxy]acetate.

EXAMPLE 111

[(5,6-Dichloro-9a-ethyl-3-oxo-1,2,9,9a-tetrahydro-3H-fluoren-7-yl)oxy]acetic acid hydrazide By conducting a reaction as described in Example 106, except that an equimolar quantity of anhydrous hydrazine is used in place of the ammonium hydroxide, there is obtained [(5,6-dichloro-9a-ethyl-3-oxo-1,2,9,9a-tetrahydro-3H-fluoren-7-yl)oxy]acetic acid hydrazide.

By carrying out a reaction as described in Example 70, Step B, except the 2-hydroxyisobutyric acid is replaced by an equimolar amount of:

EXAMPLE 112:

2-Ethyl-2-hydroxybutyric acid

EXAMPLE 113:

L(+)-lactic acid

EXAMPLE 114:

5-Hydroxypentanoic acid

EXAMPLE 115:

1-Hydroxycyclobutanecarboxylic acid

EXAMPLE 116:

1-Hydroxycyclopentanecarboxylic acid

There is obtained:

EXAMPLE 112:

1-Carboxy-1-ethylpropyl (+) [(5,6-dichloro-9a-ethyl-3-oxo-1,2,9,9a-tetrahydro-3H-fluoren-7-yl)oxy]acetate.

EXAMPLE 113:

L(+)1-Carboxyethyl (+) [(5,6-dichloro-9a-ethyl-3-oxo-1,2,9,9a-tetrahydro-3H-fluoren-7-yl)oxy]acetate.

EXAMPLE 114:

4-Carboxybutyl (+) [(5,6-dichloro-9a-ethyl-3-oxo-1,2,9,9a-tetrahydro-3H-fluoren-7-yl)oxy]acetate.

EXAMPLE 115:

1-Carboxycyclobutyl (+) [(5,6-dichloro-9a-ethyl-3-oxo-1,2,9,9a-tetrahydro-3H-fluoren-7-yl)oxy]acetate.

EXAMPLE 116:

1-Carboxycyclopentyl (+) [(5,6-dichloro-9a-ethyl-3-oxo-1,2,9,9a-tetrahydro-3H-fluoren-7-yl)oxy]acetate.

EXAMPLE 117

Parenteral Solution of the Sodium Salt of (+) [(5,6-dichloro-9a-ethyl-3-oxo-1,2,9,9a-tetrahydro-3H-fluoren-7-yl)oxy]acetic acid.

(+) [(5,6-Dichloro-9a-ethyl-3-oxo-1,2,9,9a-tetrahydro-3H-fluoren-7-yl)oxy]acetic acid (Example 31, Step A) (100 mg) is dissolved by stirring and warming in a solution of 0.05 N sodium bicarbonate (6 ml). The solution is then diluted to 10 ml. and sterilized by filtration. All the water used in the preparation is pyrogen-free.

EXAMPLE 118

Parenteral Solution of the Sodium Salt of (+) [(5,6-dichloro-3-oxo-9a-propyl-1,2,9,9a-tetrahydro-3H-fluoren-7-yl)oxy]acetic acid.

(+) [(5,6-dichloro-3-oxo-9a-propyl-1,2,9,9a-tetrahydro-3H-fluoren-7-yl)oxy]acetic acid (Example 37, Step A) (100 mg) is dissolved by stirring and warming in a solution of 0.05 N sodium bicarbonate (6 ml). The solution is then diluted to 10 ml. and sterilized by filtration. All the water used in the preparation is pyrogen-free.

EXAMPLE 119

Parenteral Solution of the Sodium Salt of (+) [(5,6-dichloro-3-oxo-9a-propargyl-1,2,9,9a-tetrahydro-3H-fluoren-7-yl)oxy]acetic acid.

(+)[(5,6-Dichloro-3-oxo-9a-propargyl-1,2,9,9a-tetrahydro-3H-fluoren-7-yl)oxy]acetic acid (Example 34, Step A) (100 mg) is dissolved by stirring and warming in a solution of 0.05 N sodium bicarbonate (6 ml). The solution is then diluted to 10 ml. and sterilized by filtration. All the water used in the preparation is pyrogen-free.

EXAMPLE 120

Parenteral solution of the Sodium Salt of (+) [(5,6-dichloro-9a-cyclopropyl-3-oxo-1,2,9,9a-tetrahydro-3H-fluoren-7-yl)oxy]acetic acid.

(+) [(5,6-Dichloro-9a-cyclopropyl-3-oxo-1,2,9,9a-tetrahydro-3H-fluoren-7-yl)oxy]acetic acid (Example 43, Step A) (100 mg) is dissolved by stirring and warming in a solution of 0.05 N sodium bicarbonate (6 ml). The solution is then diluted to 10 ml. and sterilized by filtration. All the water used in the preparation is pyrogen-free.

EXAMPLE 121

Parenteral Solution of the Sodium Salt of (+) [(9a-allyl-5,6-dichloro-3-oxo-1,2,9,9a-tetrahydro-3H fluoren-7-yl)oxy]acetic acid.

(+) [(9a-allyl-5,6-dichloro-3-oxo-1,2,9,9a-tetrahydro-3H-fluoren-7-yl)oxy]acetic acid (Example 33, Step A) (100 mg.) is dissolved in 0.05 N sodium bicarbonate solution (6 ml.) by warming and stirring. The solution is then diluted to 10 ml with water and sterilized by filtration. All the water used in the preparation is pyrogen-free.

EXAMPLE 122

Parenteral Solution of the 1-Methylpiperazinium Salt of (+) [(9a-benzyl-5,6-dichloro-3-oxo-1,2,9,9a-tetrahydro-3H-fluoren-7-yl)oxy]acetic acid.

(+) [(9a-Benzyl-5,6-dichloro-3-oxo-1,2,9,9a-tetrahydro-3H-fluoren-7-yl)oxy]acetic acid (100 mg.) Example 36, Step A) is dissolved by warming and stirring in a solution of 0.05 N 1-methylpiperazine (6 ml). The solution is then diluted to 10 ml with water and sterilized by filtration. All the water used in the preparation is pyrogen-free.

Similar parenteral solutions can be prepared by replacing the active ingredient of the above example by any of the other carboxylic acid compounds of this invention.

EXAMPLE 123

Parenteral Solution of the Sodium Salt of 1-Carboxy-1-methylethyl (+) [(5,6-dichloro-9a-ethyl-3-oxo-1,2,9,9a-tetrahydro-3H-fluoren-7-yl)oxy]acetate 1-Carboxy-1-methylethyl (+) [(5,6-Dichloro-9a-ethyl-3-oxo-1,2,9,9a-tetrahydro-3H-fluoren-7-yl)oxy]acetate (Example 70, Step B) (100 mg.) is dissolved by stirring and warming in a solution of 0.05 N sodium bicarbonate (6 ml). The solution is then diluted to 10 ml and sterilized. All the water used in the preparation is pyrogen-free.

EXAMPLE 124

Parenteral Solution of the Sodium Salt of 1-Carboxy-1-methylethyl (+) [(5,6-dichloro-3-oxo-9a-propyl-1,2,9,9a-tetrahydro-3H-fluoren-7-yl)oxy]acetate 1-Carboxy-1-methylethyl (+) [(5,6-Dichloro-3-oxo-9a-propyl-1,2,9,9a-tetrahydro-3H-fluoren-7-yl)oxy]acetate (Example 73) (100 mg.) is dissolved by stirring and warming in a solution of 0.05 N sodium bicarbonate (6 ml). The solution is then diluted to 10 ml and sterilized. All the water used in the preparation is pyrogen-free.

EXAMPLE 125

Parenteral Solution of the Sodium Salt of 1-Carboxy-1-methylethyl (+) [(9aa-allyl-5,6-dichloro-3-oxo-1,2,9,9aa-tetrahydro-3H-fluoren-7-yl)oxy]acetate 1-Carboxy-1-methylethyl (+) [(9aa-allyl-5,6-dichloro-3-oxo-1,2,9,9aa-tetrahydro-3H-fluoren-7-yl)oxy]acetate (Example 80) (100 mg.) is dissolved in 0.05N sodium bicarbonate solution (6 ml.) by warming and stirring. The solution is then diluted to 10 ml with water and sterilized by filtration. All the water used in the preparation is pyrogen-free.

EXAMPLE 126

Parenteral Solution of the Ammonium Salt of 1-Carboxyl-1-methylethyl (+) [(5,6-dichloro-9aa-isopropyl-3-oxo-1,2,9,9aa-tetrahydro-3H-fluoren-7-yl)oxy]acetate 1-Carboxy-1-methylethyl (+) [(5,6-dichloro-9aa-isopropyl-3-oxo-1,2,9,9aa-tetrahydro-3H-fluoren-7-yl)oxy]acetate (100 mg.) (Example 74) is dissolved by warming and stirring in a solution of 0.05N ammonium hydroxide (6 ml). The solution is then diluted to 10 ml with water and sterilized by filtration. All the water used in the preparation is pyrogen-free.

EXAMPLE 127

Dry-filled capsules containing 50 mg. of active ingredient per capsule

|  | Per Capsule |
|---|---|
| (+) [(5,6-dichloro-9a-ethyl-3-oxo-1,2,9,9a-tetrahydro-3H-fluoren-7-yl)oxy]-acetic acid | 50 mg. |
| Lactose | 149 mg. |
| Magnesium Stearate | 1 mg. |
| Capsule (Size No. 1) | 200 mg. |

The (+) [(5,6-dichloro-9aa-ethyl-3-oxo-1,2,9,9aa-tetrahydro-3H-fluoren-7-yl)oxy]acetic acid (Example 31, Step A) is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 128

Dry-filled capsules containing 50 mg. of active ingredient per capsule

|  | Per Capsule |
|---|---|
| (+) [(5,6-dichloro-3-oxo-9a-propyl-1,2,9,9a-tetrahydro-3H-fluoren-7-yl)oxy]-acetic acid | 50 mg. |
| Lactose | 149 mg. |
| Magnesium Stearate | 1 mg. |
| Capsule (Size No. 1) | 200 mg. |

The (+) [(5,6-dichloro-3-oxo-9aa-propyl-1,2,9,9aa-tetrahydro-3H-fluoren-7-yl)oxy]acetic acid (Example 37, Step A) is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 129

Dry-Filled Capsules Containing 50 mg. of Active Ingredient Per Capsule

|  | Per Capsule |
|---|---|
| 1-Carboxy-1-methylethyl (+) [(5,6-dichloro-9a-ethyl-3-oxo-1,2,9,9a-tetrahydro-3H-fluoren-7-yl)oxy]acetate | 50 mg. |
| Lactose | 49 mg. |
| Magnesium Stearate | 1 mg. |
| Capsule (Size No. 1) | 100 mg. |

The 1-carboxy-1-methylethyl (+) [(5,6-dichloro-9aa-ethyl-3-oxo-1,2,9,9aa-tetrahydro-3H-fluoren-7-yl)oxy]acetate (Example 70, Step B) is reduced to a No. 60 powder and then lactose and magnesium stearate are passed through a No. 60 bolting cloth onto the powder and the combined ingredients admixed for 10 minutes and then filled into a No. 2 dry gelatin capsule.

EXAMPLE 130

Dry-Filled Capsules Containing 50 mg. of Active Ingredient Per Capsule

|  | Per Capsule |
|---|---|
| 1-Carboxy-1-methylethyl(+)[(5,6-dichloro-3-oxo-9a-propyl-1,2,9,9a-tetrahydro-3H-fluoren-7-yl)oxy]acetate | 50 mg. |
| Lactose | 49 mg. |
| Magnesium Stearate | 1 mg. |
| Capsule (Size No. 1) | 100 mg. |

The 1-carboxy-1-methylethyl (+) [(5,6-dichloro-3-oxo-9aa-propyl-1,2,9,9aa-tetrahydro-3H-fluoren-7-yl)oxy]acetate (Example 73) is reduced to a No. 60 powder and then lactose and magnesium stearate are passed through a No. 60 bolting cloth onto the powder and the combined ingredients admixed for 10 minutes and then filled into a No. 2 dry gelatin capsule.

Similar dry-filled capsules can be prepared by replacing the active ingredient of the above example by any of the other compounds of this invention.

What is claimed is:

1. A compound of the formula:

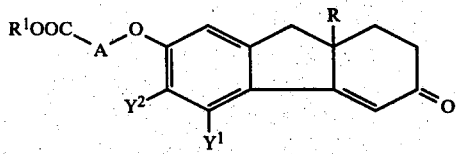

wherein
R is $C_2$ to $C_4$ alkenyl, branched or unbranched; $R^1$ is H, lower alkyl, lower alkenyl, loweralkynyl, lower cycloalkyl; substituted lower alkyl, where the substituent is carboxy, lower alkoxycarbonyl, oxo, hydroxy, lower alkoxy, halo, lower acyloxy, lower dialkylamino, sulfamoyl, pyridyl, furyl, tetrahydrofuryl, aryl, 1-methylpiperazinyl, and thienyl; substituted cycloalkyl; a heterocyclic moiety selected from the group consisting of imidazolyl, pyridyl, thiazolyl, pyrazinyl, and furyl; and aryl; $Y^1$ and $Y^2$ are independently Cl and $CH_3$; A is $(CH_2)_2$ or

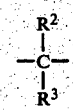

where $R^2$ is H, methyl or ethyl, $R^3$ is H, F or methyl and $R^2$ and $R^3$, may be joined together to form the ring $>C(CH_2)_n$ where n is the integer 2, 3 or 4; and pharmaceutically acceptable salts thereof.

2. A compound according to claim 1 wherein R is vinyl.

3. A compound according to claim 1 where R is allyl.

4. A compound according to claim 1 where $R^1$ is hydrogen.

5. A compound according to claim 1 where $R^1$ is carboxyloweralkyl.

6. A compound of claim 1 where $R^1$ is 1-carboxy-1-methylethyl.

7. A compound according to claim 1 where $Y^1$ and $Y^2$ are Cl.

8. A compound according to claim 1 where A is

and $R^2$ and $R^3$ are H.

9. A compound according to claim 1 which is [(5,6-dichloro-3-oxo-9a-vinyl-1,2,9,9a-tetrahydro-3H-fluoren-7-yl)oxy]acetic acid.

10. A compound which is the (+) enantiomer of [(5,6-dichloro-3-oxo-9a-vinyl-1,2,9,9a-tetrahydro-3H-fluoren-7-yl)oxy]acetic acid.

11. A compound which is [(9a-allyl-5,6-dichloro-3-oxo-1,2,9,9a-tetrahydro-3H-fluoren-7-yl)oxy]acetic acid.

12. A compound which is the (+) enantiomer of [(9a-allyl-5,6-dichloro-3-oxo-1,2,9,9a-tetrahydro-3H-fluoren-7-yl)oxy]acetic acid.

13. A compound which is the (+) enantiomer of 1-carboxy-1-methylethyl [(5,6-dichloro-3-oxo-9a-vinyl-1,2,9,9a-tetrahydro-3H-fluoren-7-yl)oxy]acetate.

14. A compound which is the (+) enantiomer of 1-carboxy-1-methylethyl [(9a-allyl-5,6-dichloro-3-oxo-1,2,9,9a-tetrahydro-3H-fluoren-7-yl)oxy]acetate.

15. A composition in unit dosage form for the treatment of grey matter edema comprising a compound of the formula:

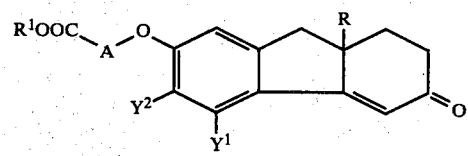

wherein
R is $C_2$ to $C_4$ alkenyl, branched or unbranched; $R^1$ is H, lower alkyl, lower alkenyl, loweralkynyl, lower cycloalkyl; substituted lower alkyl, where the substituent is carboxy, lower alkoxycarbonyl, oxo, hydroxy, lower alkoxy, halo, lower acyloxy, lower dialkylamino, sulfamoyl, pyridyl, furyl, tetrahydrofuryl, aryl, 1-methylpiperidyl, morpholinyl, pyrrolidinyl, 1-methylpiperazinyl, and thienyl; substituted cycloalkyl; a heterocyclic moiety selected from the group consisting of imidazolyl, pyridyl, thiazolyl, pyrazinyl, and furyl; and aryl;
$Y^1$ and $Y^2$ are independently Cl and $CH_3$;
A is $(CH_2)_2$ or

where $R^2$ is H, methyl or ethyl, $R^3$ is H, F or methyl and $R^2$ and $R^3$, may be joined together to form the ring $C(CH_2)_n$ where n is the integer 2, 3 or 4; and pharmaceutically acceptable salts thereof.

* * * * *

UNITED STATES PATENT AND TRADEMARK OFFICE
CERTIFICATE OF CORRECTION

PATENT NO. : 4,356,314

DATED : October 26, 1982

INVENTOR(S) : Edward J. Cragoe, Jr.; Gerald E. Stokker & Norman P. Gould

It is certified that error appears in the above—identified patent and that said Letters Patent is hereby corrected as shown below:

Claim 1, line 16, after "aryl" insert -- 1-methylpiperidyl, morpholinyl, pyrrolidinyl, --.

Signed and Sealed this

Twenty-second Day of February 1983

[SEAL]

Attest:

GERALD J. MOSSINGHOFF

Attesting Officer

Commissioner of Patents and Trademarks